(12) United States Patent
Winchell et al.

(10) Patent No.: US 9,260,762 B2
(45) Date of Patent: Feb. 16, 2016

(54) REAL TIME PCR ASSAY FOR DETECTION OF BACTERIAL RESPIRATORY PATHOGENS

(75) Inventors: Jonas M. Winchell, Lilburn, GA (US); Agnes Warner, Lilburn, GA (US); Kathleen Thurman, Elijay, GA (US)

(73) Assignee: The United States of America as represented by the Secretary of the Department of Health and Human Services, Centers for Disease Control and Prevention, Washington, DC (US)

( * ) Notice: Subject to any disclaimer, the term of this patent is extended or adjusted under 35 U.S.C. 154(b) by 383 days.

(21) Appl. No.: 13/641,444

(22) PCT Filed: Apr. 15, 2011

(86) PCT No.: PCT/US2011/032749
§ 371 (c)(1),
(2), (4) Date: Nov. 28, 2012

(87) PCT Pub. No.: WO2011/133433
PCT Pub. Date: Oct. 27, 2011

(65) Prior Publication Data
US 2013/0065787 A1    Mar. 14, 2013

Related U.S. Application Data

(60) Provisional application No. 61/324,986, filed on Apr. 16, 2010.

(51) Int. Cl.
*C12P 19/34* (2006.01)
*C12Q 1/68* (2006.01)

(52) U.S. Cl.
CPC .................................. *C12Q 1/689* (2013.01)

(58) Field of Classification Search
None
See application file for complete search history.

(56) References Cited

U.S. PATENT DOCUMENTS

| | | | |
|---|---|---|---|
| 5,474,796 A * | 12/1995 | Brennan | 427/2.13 |
| 6,582,908 B2 * | 6/2003 | Fodor et al. | 506/9 |
| 6,773,882 B2 * | 8/2004 | Hogan et al. | 435/6.15 |
| 7,659,388 B2 | 2/2010 | Oh et al. | |
| 7,794,944 B2 | 9/2010 | Felden | |
| 7,972,777 B1 * | 7/2011 | Barry et al. | 435/6.12 |
| 2002/0197611 A1 * | 12/2002 | Chagovetz | 435/6 |
| 2007/0116726 A1 * | 5/2007 | Ratti et al. | 424/263.1 |
| 2007/0212378 A1 * | 9/2007 | Baseman et al. | 424/264.1 |
| 2009/0092969 A1 | 4/2009 | Aye et al. | |
| 2009/0318300 A1 * | 12/2009 | Perera et al. | 506/7 |
| 2013/0331285 A1 | 12/2013 | Winchell et al. | |

FOREIGN PATENT DOCUMENTS

| | | |
|---|---|---|
| EP | 0943691 | 9/1999 |
| EP | 1179090 | 4/2010 |
| JP | 2007228977 | 9/2007 |
| WO | WO 99/27105 | 6/1999 |
| WO | WO 00/70086 | 11/2000 |
| WO | WO 2005/032491 | 4/2005 |
| WO | WO 2009/048873 | 4/2009 |
| WO | WO 2013/187958 | 12/2013 |

OTHER PUBLICATIONS

Diffenbach (PCR methods and Applications (1993) vol. 3, pp. S30-S37).*
Roux et al (PCR Methods and Applications (1995) vol. 4, pp. s185-s194).*
Bonanomi et al., "Monitoring Intracellular Replication of *Chlamydophila* (*Chlamydia*) *pneumoniae* in Cell Cultures and Comparing Clinical Samples by Real-Time PCR," *Diagnostic Microbiology and Infectious Disease*, vol. 46, pp. 39-47, 2003.
EMBL Database Accession No. AB422799, 2008 (1 page).
EMBL Database Accession No. DJ127835, 2008 (1 page).
EMBL Database Accession No. HA435426, 2009 (1 page).
Genseq Database Accession No. AAX94942, 1999 (1 page).
Genseq Database Accession No. ACH00715, 2004 (1 page).
Genseq Database Accession No. ADJ88236, 2004 (1 page).
Genseq Database Accession No. ADZ21250, 2005 (1 page).
Genseq Database Accession No. ATH55869, 2008 (1 page).
Ginevra et al., "Development and Evaluation of Chlamylege, a New Commercial Test Allowing Simultaneous Detection and Identification of *Legionella*, *Chlamydophila pneumoniae*, and *Mycoplasma pneumoniae* in Clinical Respiratory Specimens by Multiplex PCR," *Journal of Clinical Microbiology*, vol. 43, pp. 3247-3254, 2005.
Gullsby et al., "Simultaneous Detection of *Chlamydophila pneumoniae* and *Mycoplasma pneumoniae* by Use of Molecular Beacons in a Duplex Real-Time PCR," *Journal of Clinical Microbiology* vol. 46, pp. 727-731, 2008.
Higgins et al., "Verification of the ProPneumo-I assay for the simultaneous detection of *Mycoplasma pneumoniae* and *Chlamydophila pneumoniae* in clinical respiratory specimens," *Annals of Clinical Microbiology and Antimicrobials*, vol. 8:10, 2009 (9 pages).
Khanna et al., "The Pneumoplex Assays, a Multiplex PCR-Enzyme Hybridization Assay That Allows Simultaneous Detection of Five Organisms, *Mycoplasma pneumoniae*, *Chlamydia* (*Chlamydophila*) *pneumoniae*, *Legionella pneumophila*, *Legionella micdadei*, and *Bordetella pertussis*, and Its Real-Time Counterpart," *Journal of Clinical Microbiology* vol. 43, pp. 565-571, 2005.

(Continued)

*Primary Examiner* — Katherine Salmon
(74) *Attorney, Agent, or Firm* — Klarquist Sparkman, LLP

(57) ABSTRACT

Methods for detecting *Mycoplasma pneumoniae*, *Chlamydophila pneumoniae*, and *Legionella* spp. are disclosed. A sample suspected of containing a nucleic acid of one or more of *M. pneumoniae*, *C. pneumoniae*, and *Legionella* spp. is screened for the presence or absence of that nucleic acid. Determining whether the *M. pneumoniae*, *C. pneumoniae*, or *Legionella* spp. nucleic acid is present in the sample can be accomplished by detecting hybridization between a *M. pneumoniae* probe (such as a CARDS toxin probe), a *C. pneumoniae* probe (such as a ArgR probe), or a *Legionella* spp. probe (such as a SsrA probe) and a nucleic acid in a sample. Also disclosed are probes and primers for the detection of *M. pneumoniae*, *C. pneumoniae*, and *Legionella* spp., and kits that contain the disclosed probes and/or primers.

11 Claims, 5 Drawing Sheets

(56) References Cited

OTHER PUBLICATIONS

Kumar et al, "Detection of 11 Common Viral and Bacterial Pathogens Causing Community-Acquired Pneumonia or Sepsis in Asymptomatic Patients by Using a Multiplex Reverse Transcription-PCR Assay with Manual (Enzyme Hybridization) or Automated (Electronic Microarray) Detection," *Journal of Clinical Microbiology* vol. 46, pp. 3063-3072, 2008.

McDonough et al., "A Multiplex PCR for Detection of *Mycoplasma pneumoniae, Chlamydophila pneumoniae, Legionella pneumophila,* and *Bordetella pertussis* in Clinical Specimens," *Molecular and Cellular Probes*, vol. 19, pp. 314-322, 2005.

Miyashita et al., "Multiplex PCR for the simultaneous detection of *Chlamydia pneumoniae, Mycoplasma pneumoniae* and *Legionella pneumophila* in community-acquired pneumonia," *Respiratory Medicine* vol. 98, pp. 542-550, 2004.

Morozumi et al., "Simultaneous Detection of Pathogens in Clinical Samples from Patients with Community-Acquired Pneumonia by Real-Time PCR with Pathogen-Specific Molecular Beacon Probes," *Journal of Clinical Microbiology* vol. 44, pp. 1440-1446, 2006.

Pinar et al., "Rapid Detection of Bacterial Atypical Pneumonia Agents by Multiplex PCR," *Cent. Eur. J. Publ. Health* vol. 12, pp. 3-5, 2004.

Raggam et al., "Single-Run, Parallel Detection of DNA from Three Pneumonia-Producing Bacteria by Real-Time Polymerase Chain Reaction," *Journal of Molecular Diagnostics* vol. 7, pp. 133-138, 2005.

Thurman et al., "Detection of *Mycoplasma pneumoniae, Chlamydia pneumoniae,* and *Legionella* spp. in Clinical Specimens Using a Single-Tube Multiplex Real-Time PCR Assay," *Diagnostic Microbiology and Infectious Disease*, vol. 70, pp. 1-9, 2011.

Welti et al., "Development of a multiplex real-time PCR assay to detect *Chlamydia pneumoniae, Legionella pneumophila* and *Mycoplasma pneumoniae* in respiratory tract secretions," *Diagnostic Microbiology and Infectious Disease*, vol. 45, pp. 85-95, 2003.

Winchell et al., "Evaluation of Three Real-Time PCR Assays for Detection of *Mycoplasma pneumoniae* in an Outbreak Investigation," *Journal of Clinical Microbiology*, vol. 46, pp. 3116-3118, 2008.

Benitez and Winchell, "Rapid Detection and Speciation of Pathogenic Non-pneumophila *Legionella* Species Using a Multiplex Real-time PCR Assay," 113th General Meeting of the American Society for Microbiology, May 18-21, 2013 (Abstract, 1 page).

Benitez et al., "Clinical Application of a Multiplex Real-Time PCR Assay for Simultaneous Detection of *Legionella* Species, *Legionella pneumophila*, and *Legionella pneumophila* Serogroup 1," *Journal of Clinical Microbiology*, vol. 51, No. 1, pp. 348-351, 2013.

Degtyar et al., "A *Legionella* effector acquired from protozoa is involved in sphingolipids metabolism and is targeted to the host cell mitochondria," *Cellular Microbiology*, vol. 11, No. 8, pp. 1219-1235, 2009.

Feldman et al., "A Specific Genomic Location within the *icm/dot* Pathogenesis Region of Different *Legionella* Species Encodes Functionally Similar but Nonhomologous Virulence Proteins," *Infection and Immunity*, vol. 72, No. 8, pp. 4503-4511, 2004.

Feldman et al., "Coevolution between nonhomologous but functionally similar proteins and their conserved partners in the *Legionella* pathogenesis system," *PNAS*, vol. 102, No. 34, pp. 12206-12211, 2005.

Merault et al., "Specific Real-time PCR for Simultaneous Detection and Identification of *Legionella pneumophila* Serogroup 1 in Water and Clinical Samples," *Appl. Environ. Microbiol.*, vol. 77, pp. 1708-1717, 2011.

Ratcliff et al., "Sequence-Based Classification Scheme for the Genus *Legionella* Targeting the *mip* Gene," *J. Clin. Microbiol.*, vol. 36, pp. 1560-1567, 1998.

Stolhaug and Bergh, "Identification and Differentiation of *Legionella pneumophila* and *Legionella* spp. with Real-time PCR Targeting the 16S rRNA Gene and Species Identification by *mip* Sequencing," *Appl. Environ. Microbiol.*, vol. 72, pp. 6394-6398, 2006.

Su et al, "Identification of *Legionella* Species by Use of an Oligonucleotide Array," *Journal of Clinical Microbiology*, vol. 47, No. 5, pp. 1386-1392, 2009.

Zhou et al., "PCR methods for the rapid detection and identification of four pathogenic *Legionella* spp. and two *Legionella pneumophila* subspecies based on the gene amplification of *gyrB*," *App. Microbiol. Biotechnol.*, vol. 91, pp. 777-787, 2011.

\* cited by examiner

```
                            SEQUENCE LISTING

<160> NUMBER OF SEQ ID NOS: 21

<210> SEQ ID NO 1
<211> LENGTH: 1779
<212> TYPE: DNA
<213> ORGANISM: Mycoplasma pneumoniae

<400> SEQUENCE: 1
atgccaaatc ctgttagatt tgtttaccgt gttgatttga gaagccctga agaaatttt       60 gaacatggct tttcaacttt aggtgatgtg agaaatttct ttgaacacat tctctccact     120
aattttggta gaagctattt tatttccact tcagaaacac ccacagcagc tattcgcttc     180
tttggtagct ggttacggga atatgtacca gagcacccca gaagggctta cttatatgaa     240
attcgtgccg accaacactt ttacaatgcc cgcgccactg gggagaactt gttagattta     300
atgcgtcaaa gacaagtagt atttgactct ggtgatcgag aaatggcaca aatgggaatt     360
agagctttac gcacttcctt tgcgtatcaa cgtgaatggt ttaccgatgg tccaattgca     420
gcagctaatg tccgtagtgc ttgactagta gatgctgttc ccgttgaacc tggtcatgct     480
caccacccgg ctggtcgtgt tgtagagact actagaatta atgaaccgga aatgcacaac     540
cctcattatc aagagctgca aacccaagcc aatgatcaac catgattgcc aacaccagga     600
atagctactc ctgtacattt atcaattccc caagcagctt ccgttgctga tgtttcggaa     660
ggtacttccg cttcgctatc gtttgcgtgc cctgattgaa gtccaccttc tagtaatggt     720
gaaaatccgc tagacaaatg cattgcggaa aagattgata actataacct acaatcctta     780
ccacagtacg ctagcagtgt aaaggaactg gaagatacac cagtatacct aaggggaatt     840
aaaacgcaaa aaaccttat gttacaagca gatccgcaaa ataacaatgt cttttggtc      900 gaagtaaacc ccaaacaaaa gtccagcttt ccccaaacca tcttctttg ggatgtttat      960 caacgaattt gtctcaagga tttaactggt gcacaaatca gtctttcgct tactgccttt    1020
actactcagt atgctggtca gctcaaagtg caccttagtg ttagcgcggt taatgccgtg    1080
aaccaaaagt gaaaatgac accgcaagac attgcaataa ctcagtttcg ggtctcctct     1140
gaactgttag gtcaaactga aaatggcttg ttctgaaata ccaagagtgg tggttcacaa    1200
cacgatttgt atgtatgtcc tttgaaaaat ccacctagtg atttggaaga attacaaata    1260
attgttgatg aatgtactac ccatgcgcag tttgttacta tgcgtgcagc tagcaccttc    1320
tttgttgatg ttcagctagg ctggtattga aggggttatt actataccc acaattaagt    1380 ggttgatctt atcagatgaa aacaccagat ggacagatat tctatgatct aaaaacttcg    1440
aaaatcttct ttgtccagga caaccaaaac gtgttctttc tccataataa actcaacaaa    1500
caaactggtt acagctggga ttgagtagaa tggctaaaac atgacatgaa tgaggacaaa    1560
gacgaaaact ttaaatggta cttttcgcgt gatgacctta ccattccttc cgttgaaggg    1620
cttaacttcc gccacattcg ctgttacgct gacaaccagc agttaaaggt gatcataagc    1680
ggttcacgtt ggggcggttg gtactccact tacgataaag ttgaaagtaa tgtcgaagat    1740
aagattttgg tcaaagatgg ttttgatcgc ttttagcga                           1779
```

<210> SEQ ID NO 2
<211> LENGTH: 444
<212> TYPE: DNA
<213> ORGANISM: Chlamydophila pneumoniae

<400> SEQUENCE: 2

```
atgaaaaaaa aagtaactat agatgaggct ttaaaagaaa ttttacgtct tgaaggagcg    60
gcaactcagg aggaattatg tgcaaaactc ttagctcaag gttttgctac aacccagtcg   120
tctgtatctc gttggctacg aaagattcag gctgtaaagg ttgctggaga gcgtggtgct   180
cgttattctt taccctcttc aacagagaag accacgaccc gtcatttggt gctctctatt   240
cgccataacg cctctcttat tgtaattcgt acggttcctg gttcagcttc ttggatcgct   300
gctttgttag atcaagggct caaagatgaa attcttggaa cttttggcagg agatgacacg   360
atttttgtca ctcctataga tgaagggagg ctcccattgt tgatggtttc gattgcaaat   420
ttactgcaag ttttcttgga ttaa                                         444
```

<210> SEQ ID NO 3
<211> LENGTH: 362
<212> TYPE: DNA
<213> ORGANISM: Legionella pneumophila

<400> SEQUENCE: 3

```
gtgggttgca aaccggaaag tgcatgccga gaaggagatc tctcgtaaat aagactcaat    60
taaatataaa tgcaaacgat gaaaactttg ctggtgggga agctatcgct gcctaataag   120
cactttagtt aaaccatcac tgtgtactgg ccaataaacc cagtatcccg ttcgaccgag   180
cccgcttatc ggtatcgaat caacggtcat aagagataag ctagcgtcct aatctatccc   240
gggttatggc gcgaaactca gggaatcgct gtgtatcatc ctgcccgtcg gaggagccac   300
agttaaattc aaaagacaag gctatgcatg tagagctaaa ggcagaggac ttgcggacgc   360
gg                                                                 362
```

<210> SEQ ID NO 4
<211> LENGTH: 2371
<212> TYPE: DNA
<213> ORGANISM: Homo sapiens

<400> SEQUENCE: 4

```
agactggcgc gcgcggacgg tcatgggact tcagcatggc ggtgtttgca gatttggacc    60
tgcgagcggg ttctgacctg aaggctctgc gcggacttgt ggagacagcc gctcaccttg   120
gctattcagt tgttgctatc aatcatatcg ttgactttaa ggaaaagaaa caggaaattg   180
aaaaaccagt agctgtttct gaactcttca caactttgcc aattgtacag ggaaaatcaa   240
gaccaattaa aattttaact agattaacaa ttattgtctc ggatccatct cactgcaatg   300
ttttgagagc aacttcttca agggcccggc tctatgatgt tgttgcagtt tttccaaaga   360
cagaaaagct ttttcatatt gcttcacac atttagatgt ggatttagtc tgcataactg   420
taacagagaa actaccattt tacttcaaaa gacctcctat taatgtggcg attgaccgag   480
gcctggcttt tgaacttgtc tatagccctg ctatcaaaga ctcccacaatg agaaggtata   540
caatttccag tgccctcaat tgatgcaaaa tctgcaaagg aaagaatgta attatatcta   600
gtgctgcaga aaggccttta gaaataagag ggcatatga cgtggcaaat ctaggcttgc   660
tgtttgggct ctctgaaagt gacgccaagg ctgcggtgtc caccaactgc cgagcagcgc   720
ttctccatgg agaaactaga aaactgcttt ttggaattat ctctacagtg aagaaacctc   780
```

-continued

```
ggccatcaga aggagatgaa gattgtcttc cagcttccaa gaaagccaag tgtgagggct      840
gaaaagaatg ccccagtctc tgtcagcact cccttcttcc cttttatagt tcatcagcca      900
caacaaaaat aaaacctttg tgtgatttac tgttttcatt tggagctaga aatcaatagt      960
ctataaaaac agtttaactt gcaatccatt aaaacaacaa acgaaaccta gtgaagcatc     1020 ttttaaaag gctgccagct taatgaattt agatgtactt taagagagaa agactggtta     1080
tttctccttt tgtgtaagtga taaacaacag caaatatact tgaataaaat gtttcaggta     1140
tttttgtttc attttgtttt tgagataggg tctttgttgc tcaggctgga gtacagtggc     1200
ataatcacag ctcactgcaa cctcaatcct gggctcaagt gatcctcccg cttcagcctc     1260
tcaagcagcg ggaactacag gtgtgcacta ccacacctgg ctattttttt tttttttttt     1320
tttttccctt gtagagacat ggtctcacta tgttgctgag gctggtctca aactcctagg     1380
atcaagccat cctcccgctt tggcctccta aagtgctggg attacatgag ccaccacatg     1440
cagccagatg tttgaatatt ttaagagctt cttttcgaaag tttcttgttc atactcaaat     1500
agtagttatt ttgaagatat tcaaacttat attgaagaag tgacttttagt tcctcttgtt     1560 ttaagcttct ttcatgtatt caaatcagca tttttttcta agaaattgct atagaatttg     1620
tggaaggaga gaggatacac atgtaaaatt acatctggtc tcttccttca ctgcttcatg     1680
cctacgtaag gtctttgaaa taggattcct tacttttagt tagaaacccc taaaacgcta     1740
atattgattt tcctgatagc tgtattaaaa atagcaaagc atcggactga accaactttg     1800
gaaataattt attttataa tgggatcatg ttaagtagaa gtagcttttt atgcaaatac     1860
atgcatttat gcaatattaa tgtaagggct ctaaaacaat ggagtagagc cagaggtata     1920
actgaataag aaatttttt aagcaagaga aagacaactg ttctgcgggt tggagaaaat     1980 acaattttt tttttttt tgagacagtc tcgctctgtc ccccaggctg gagtgcagtg     2040
gctcgatctc tgctcactgc aagctccgcc tcctgggttc atgccattct cctgcctcag     2100
cctcctgagt agctgggact acaggcgctc gccatgtatt tagcagagac ggggtttcac     2160
cgtgttagcc aggatggtct caatctcctg acctcatatt ccacccgcct cggcctccca     2220
aagtgctggg attacaggcg ttagccactg cgccccggccc gagaaaatac agttttaaaa     2280
agagaaagct ttataacctc accaatgaat acaaatgttt aaataaaata ttgattaaaa     2340
aaacattaaa agtaaaaaaa aaaaaaaaa a                                    2371
```

<210> SEQ ID NO 5
<211> LENGTH: 22
<212> TYPE: DNA
<213> ORGANISM: Artificial Sequence
<220> FEATURE:
<223> OTHER INFORMATION: Synthetic oligonucleotide primer - MP181-F

<400> SEQUENCE: 5
tttggtagct ggttacggga at          22

<210> SEQ ID NO 6
<211> LENGTH: 23
<212> TYPE: DNA
<213> ORGANISM: Artificial Sequence
<220> FEATURE:
<223> OTHER INFORMATION: Synthetic oligonucleotide primer - MP181-R

<400> SEQUENCE: 6
ggtcggcacg aatttcatat aag          23

```
<210> SEQ ID NO 7
<211> LENGTH: 25
<212> TYPE: DNA
<213> ORGANISM: Artificial Sequence
<220> FEATURE:
<223> OTHER INFORMATION: Synthetic oligonucleotide probe - MP181-P

<400> SEQUENCE: 7
tgtaccagag cacccagaa gggct                                          25

<210> SEQ ID NO 8
<211> LENGTH: 23
<212> TYPE: DNA
<213> ORGANISM: Artificial Sequence
<220> FEATURE:
<223> OTHER INFORMATION: Synthetic oligonucleotide primer - CP-Arg-F

<400> SEQUENCE: 8
cgtggtgctc gttattcttt acc                                           23

<210> SEQ ID NO 9
<211> LENGTH: 20
<212> TYPE: DNA
<213> ORGANISM: Artificial Sequence
<220> FEATURE:
<223> OTHER INFORMATION: Synthetic oligonucleotide primer - CP-Arg-R

<400> SEQUENCE: 9
tggcgaatag agagcaccaa                                               20

<210> SEQ ID NO 10
<211> LENGTH: 28
<212> TYPE: DNA
<213> ORGANISM: Artificial Sequence
<220> FEATURE:
<223> OTHER INFORMATION: Synthetic oligonucleotide probe - CP-Arg-P

<400> SEQUENCE: 10
cttcaacaga gaagaccacg acccgtca                                      28

<210> SEQ ID NO 11
<211> LENGTH: 14
<212> TYPE: DNA
<213> ORGANISM: Artificial Sequence
<220> FEATURE:
<223> OTHER INFORMATION: Synthetic oligonucleotide primer - Pan-Leg-F

<400> SEQUENCE: 11
ggcgacctgg cttc                                                     14

<210> SEQ ID NO 12
<211> LENGTH: 21
<212> TYPE: DNA
<213> ORGANISM: Artificial Sequence
<220> FEATURE:
<223> OTHER INFORMATION: Synthetic oligonucleotide primer - Pan-Leg-R

<400> SEQUENCE: 12
tatgaccgtt gattcgatac c                                             21

<210> SEQ ID NO 13
<211> LENGTH: 11
<212> TYPE: DNA
<213> ORGANISM: Artificial Sequence
<220> FEATURE:
<223> OTHER INFORMATION: Synthetic oligonucleotide probe - Pan-Leg-P
```

```
<220> FEATURE:
<221> NAME/KEY: misc_feature
<222> LOCATION: (2)..(2)
<223> OTHER INFORMATION: locked nucleic acid
<220> FEATURE:
<221> NAME/KEY: misc_feature
<222> LOCATION: (5)..(5)
<223> OTHER INFORMATION: locked nucleic acid
<220> FEATURE:
<221> NAME/KEY: misc_feature
<222> LOCATION: (8)..(8)
<223> OTHER INFORMATION: locked nucleic acid

<400> SEQUENCE: 13
acgtgggttg c                                                           11

<210> SEQ ID NO 14
<211> LENGTH: 19
<212> TYPE: DNA
<213> ORGANISM: Artificial Sequence
<220> FEATURE:
<223> OTHER INFORMATION: Synthetic oligonucleotide primer - RNaseP-F

<400> SEQUENCE: 14
agatttggac ctgcgagcg                                                   19

<210> SEQ ID NO 15
<211> LENGTH: 20
<212> TYPE: DNA
<213> ORGANISM: Artificial Sequence
<220> FEATURE:
<223> OTHER INFORMATION: Synthetic oligonucleotide primer - RNaseP-R

<400> SEQUENCE: 15
gagcggctgt ctccacaagt                                                  20

<210> SEQ ID NO 16
<211> LENGTH: 23
<212> TYPE: DNA
<213> ORGANISM: Artificial Sequence
<220> FEATURE:
<223> OTHER INFORMATION: Synthetic oligonucleotide probe - RNaseP-P

<400> SEQUENCE: 16
ttctgacctg aaggctctgc gcg                                              23

<210> SEQ ID NO 17
<211> LENGTH: 21
<212> TYPE: DNA
<213> ORGANISM: Artificial Sequence
<220> FEATURE:
<223> OTHER INFORMATION: Synthetic oligonucleotide probe - Legionella
      spp.

<400> SEQUENCE: 17
acgatgaaaa ctttgctggt g                                                21

<210> SEQ ID NO 18
<211> LENGTH: 1566
<212> TYPE: DNA
<213> ORGANISM: Mycoplasma pneumoniae

<400> SEQUENCE: 18
atggggttta aactcaaggg ttttggtttt ctcacactgt tcgccagtca agcatttcta      60
actgcttgct ctgctacgct aacagtagct aacactaatc acaaaaatga agtgataag      120 tttgtgattt ttgaacctca accaccattg agccaaacta tccccaaacc agaggctgaa     180
```

```
ccagttatag agcccgatgc tgttgctaca ccacctgtgc agaatgccga ggtgcaaatt    240
aagcctgaca gctccaaggg tgtttacagt cctggtttta agttcaacac taactttatt    300
cctaaagtaa atactaagta tcggccgggc tatgatctta gctttgcctt aaagtttggt    360
actagttgaa aagaagctta tggtacaggt tggttaattg actggaagga tgttaagcag    420
gacaacaaat ttactgctta cttagctacc aacctccatg tagctgatag cttacgaaat    480
aaagacgatt acaagcctta caacaaggat ggtaatcaga aggagttttt acctggcgat    540
atcaccactg aatttctttt gggtaaatac attgatgccc aaactgtgca aagttaact     600 ccagagtacc aaaatcttaa gcacctcaat aaccggaata gtgatgcatt agtttcaatt    660
caaacatcga agttaccaaa aactgcttac actgccactg actttatcaa aactgctcag    720
tacaaataca atcacatagt gagtaacaca gtttatgagt tggacttatt ccaaaatgcc    780
gtaagttacg ctgactttgc ggtgttggaa ttagagttaa atttagccaa caatcgtgac    840
cagcaaatct ttgacagttt tataaatcca gcggtaactg cttacgaaaa gctaggtaac    900
agtttgggtc tcttttccaa cctgcaatta gatcagtatg ttgatgatac ccattatcta    960
ttgggttatc cgttacttaa acgtgaaaag acgtcttact gaaacttacc acagaagggt   1020
tatagttcac cactctatga aaatagtaat aaggaagttt cgcgcataac gcgtaacatc   1080
cggaaagatg atgaaattcc aggtagtcgt ttggtacaaa atcaaattaa ctatttaccc   1140
tttgcacaaa atgaccctaa aggcgtaatg gactttagca agtatttaaa ttacgttttt   1200
aactatcacg aaaagcaata ccaacaccat ggttatggtt tattgttaga agacactgac   1260
ttcccgggtg gttccagtgg tagtccgtta tttaaccaaa acaaacagat taacagtatt   1320
tactttgcgg ctttaccaag taaaagttac ggtgtatcgc aaattctccg cgctacgcaa   1380
aacaaagaca gtccaaaaa ctacgattta atctttggtg atagcaacac caagaaatac    1440
tatgctcaat ttgctaagga gcacaaaacc cacttgtacc atcaaattct tcaaagtaac   1500
gatgaacagt tccgctttgt cgaaaacgat caaactgtaa caagtcaaac accatttaaa   1560
agctaa                                                              1566

<210> SEQ ID NO 19
<211> LENGTH: 27
<212> TYPE: DNA
<213> ORGANISM: Artificial Sequence
<220> FEATURE:
<223> OTHER INFORMATION: Synthetic oligonucleotide primer - Mp-F

<400> SEQUENCE: 19
aagaagctta tggtacaggt tggttaa                                         27

<210> SEQ ID NO 20
<211> LENGTH: 24
<212> TYPE: DNA
<213> ORGANISM: Artificial Sequence
<220> FEATURE:
<223> OTHER INFORMATION: Synthetic oligonucleotide primer - MpR

<400> SEQUENCE: 20
tggaggttgg tagctaagta agca                                            24

<210> SEQ ID NO 21
<211> LENGTH: 34
<212> TYPE: DNA
<213> ORGANISM: Artificial Sequence
<220> FEATURE:
<223> OTHER INFORMATION: Synthetic oligonucleotide primer - MpP
```

```
<400> SEQUENCE: 21
tgactggaag gatgttaagc aggacaacaa attt                           34
```

REAL TIME PCR ASSAY FOR DETECTION OF BACTERIAL RESPIRATORY PATHOGENS

CROSS REFERENCE TO RELATED APPLICATIONS

This is the §371 U.S. National Stage of International Application No. PCT/US2011/032749, filed Apr. 15, 2011, which was published in English under PCT Article 21(2), which in turn claims the benefit of U.S. Provisional Application No. 61/324,986, filed Apr. 16, 2010, which is incorporated by reference herein it its entirety.

FIELD

This disclosure concerns methods and compositions related to the detection of bacterial respiratory pathogens, particularly real-time multiplex PCR for detection of *Mycoplasma pneumoniae, Chlamydophila pneumoniae,* and *Legionella* spp.

BACKGROUND

Respiratory infections caused by the atypical pathogens *Mycoplasma pneumoniae, Chlamydophila pneumoniae* and *Legionella* spp. collectively account for approximately 15% of all reported community acquired pneumonia (CAP) cases. *M. pneumoniae* accounts for about 15-20% of all atypical CAPs. Outbreaks usually occur within a 3-7 year interval with varying incidence rates. Though symptoms are mild and individuals often do not seek medical treatment, severe extrapulmonary disease can develop if this agent is ignored or misdiagnosed. *C. pneumoniae* is an obligate intracellular bacterium that accounts for up to 10% of all atypical CAPs. Frequently misdiagnosed or undetected, *C. pneumoniae* is suspected to be of much higher incidence due to presence of antibodies in 50% of adults due to previous infection. Legionellae account for about 2-8% of atypical community-acquired pneumonia cases. Legionellosis is caused predominantly (in about 70% of all cases) by *Legionella pneumophila* Sg 1, although other serogroups (Sg 2, 4, and 6) and other species (such as *L. bozemanii, L. longbeachae* and *L. micdadei*) have been reported as disease causing agents.

Although a presumptive clinical diagnosis can often be made through symptomology, a laboratory identification determining the etiology is critical to establish the correct course of treatment. These agents are fastidious organisms that require time-consuming procedures, specialized media, and technical expertise for successful culture. Currently, several commercially available serological methods are used to identify these agents. While commonly used, these tests are neither highly sensitive nor specific, and require an acute and convalescent patient serum (paired serum) for clear identification. Frequently these tests fail to identify all acute atypical respiratory infections. Detection by culture is not an effective strategy for diagnosis, as these agents require specific media and expertise, and thus culture identification can take weeks, only allowing a retrospective diagnosis. Urinary antigen tests used to diagnose Legionnaire's disease are only specific to *L. pneumophila* Sg1, leaving out over 30% of infections caused by other *Legionella* spp.

SUMMARY

Since identification of *M. pneumoniae, C. pneumoniae,* and *Legionella* spp. infections is problematic, etiology of many CAPs remains undetermined, and prevalence may be underestimated due to lack of a sensitive, specific, and expedient diagnostic assays.

Disclosed herein are methods for detecting presence of one or more of *M. pneumoniae, C. pneumoniae,* and *Legionella* spp. nucleic acids in a sample, such as a biological sample obtained from a subject. The disclosed methods can be used to diagnose an infection with *M. pneumoniae, C. pneumoniae,* and/or *Legionella* spp. (including, but not limited to, *L. pneumophila, L. bozemanii, L. longbeachae,* or *L. micdadei*) in a subject, for example, by analyzing a biological sample from a subject to detect *M. pneumoniae* nucleic acids (such as *M. pneumoniae* CARDS toxin nucleic acid), *C. pneumoniae* nucleic acids (such as *C. pneumoniae* ArgR nucleic acid), and/or *Legionella* spp. nucleic acids (such as *Legionella* SsrA nucleic acid) using the probes and/or primers disclosed herein. The disclosed methods provide rapid, sensitive, and specific detection of these organisms, for example, utilizing a multiplex real-time PCR assay. In addition, the disclosed methods are not limited to detection of *Legionella pneumophila*, but provide for detection of multiple *Legionella* species.

In some embodiments, the method involves contacting a sample with one or more probes capable of hybridizing to a *M. pneumoniae, C. pneumoniae,* or *Legionella* spp. nucleic acid, such as a *M. pneumoniae* CARDS toxin nucleic acid (such as SEQ ID NO: 1) or a *M. pneumoniae* orf521 nucleic acid (such as SEQ ID NO: 18), a *C. pneumoniae* ArgR nucleic acid (such as SEQ ID NO: 2), or a *Legionella* spp. SsrA nucleic acid (such as SEQ ID NO: 3), under very high stringency conditions, wherein each of the probes are detectably labeled, and detecting hybridization between one or more of the probes and a nucleic acid, wherein detection of hybridization of the *M. pneumoniae* probe indicates the presence of *M. pneumoniae* nucleic acid in the sample, detection of hybridization of the *C. pneumoniae* probe indicates the presence of *C. pneumoniae* nucleic acid in the sample, and detection of hybridization of the *Legionella* spp. probe indicates the presence of *Legionella* spp. nucleic acid in the sample. In particular examples, the disclosed methods also include contacting the sample with a probe capable of hybridizing under very high stringency conditions with a human RNase P nucleic acid sequence (such as SEQ ID NO: 4), wherein the probe is detectably labeled, and detecting hybridization, wherein hybridization of the probe indicates the presence of human nucleic acid in the sample.

In specific embodiments, the probe capable of hybridizing to *M. pneumoniae* CARDS toxin nucleic acid consists essentially of the nucleic acid sequence set forth as SEQ ID NO: 7, the probe capable of hybridizing to *M. pneumoniae* CARDS toxin nucleic acid consists essentially of the nucleic acid sequence set forth as SEQ ID NO: 21, the probe capable of hybridizing to *C. pneumoniae* ArgR nucleic acid consists essentially of the nucleic acid sequence set forth as SEQ ID NO: 10, the probe capable of hybridizing to *Legionella* spp. SsrA nucleic acid consists essentially of the nucleic acid sequence set forth as SEQ ID NO: 13 or SEQ ID NO: 17, and the probe capable of hybridizing to human RNase P nucleic acid consists essentially of SEQ ID NO: 16. In specific embodiments, the disclosed probes are detectably labeled. In some examples, the probes are labeled with a donor fluorophore and an acceptor fluorophore.

In some embodiments, the disclosed methods include amplifying one or more of a *M. pneumoniae, C. pneumoniae,* and *Legionella* spp. nucleic acid, such as a *M. pneumoniae* CARDS toxin nucleic acid (such as SEQ ID NO: 1 or a portion thereof), a *M. pneumoniae* orf521 nucleic acid (such as SEQ ID NO: 18 or a portion thereof), a *C. pneumoniae* ArgR nucleic acid (such as SEQ ID NO: 2 or a portion thereof), or a *Legionella* spp. SsrA nucleic acid (such as SEQ ID NO: 3 or a portion thereof). In some examples, a primer specific for *M. pneumoniae* CARDS toxin nucleic acid includes a nucleic acid sequence at least 90% identical to SEQ ID NO: 5 or SEQ ID NO: 6. In other examples, a primer specific for *C. pneumoniae* ArgR nucleic acid includes a nucleic acid sequence at least 90% identical to SEQ ID NO: 8 or SEQ ID NO: 9. In additional examples, a primer specific for *Legionella* spp. SsrA nucleic acid includes a nucleic acid sequence at least 90% identical to SEQ ID NO: 11 or SEQ ID NO: 12. In further examples, a primer specific for *M. pneumoniae* orf521 nucleic acid includes a nucleic acid sequence at least 90% identical to SEQ ID NO: 19 or SEQ ID NO: 20. In particular examples, the disclosed methods also include amplifying human RNase P nucleic acid (such as SEQ ID NO: 4 or a portion thereof), for example utilizing a primer specific for human RNase P, such as a nucleic acid sequence at least 90% identical to SEQ ID NO: 14 or SEQ ID NO: 15.

This disclosure also provides kits for detecting one or more of *M. pneumoniae, C. pneumoniae*, and/or *Legionella* spp. in a biological sample, for example, including one or more of the probes and primers disclosed herein.

The foregoing and other features of the disclosure will become more apparent from the following detailed description, which proceeds with reference to the accompanying figures.

SEQUENCE LISTING

Figure 1A:
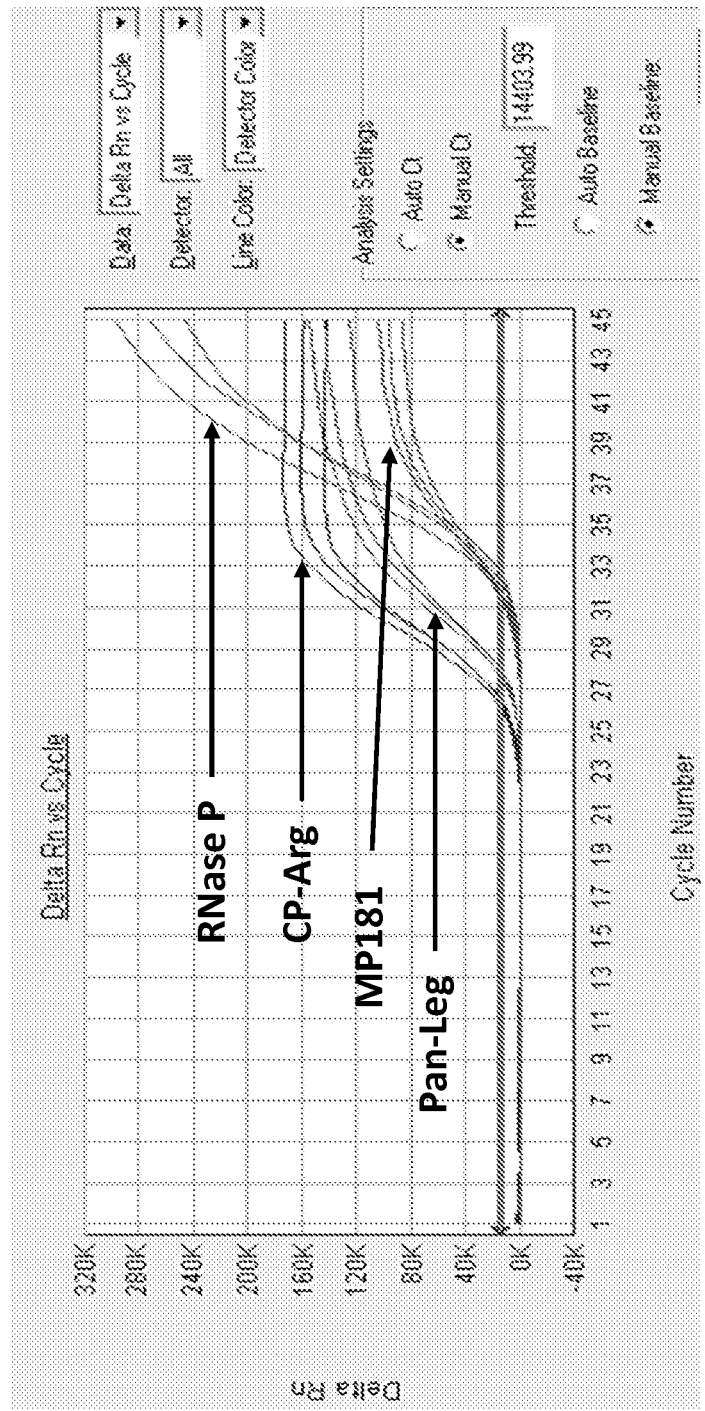
FIG. 1 is a pair of digital images showing results from multiplex real-time PCR for *M. pneumoniae* (MP181), *C. pneumoniae* (CP-Arg), *Legionella* spp. (Pan-Leg), and human RNase P (RP) in a reaction containing a combined positive control containing *M. pneumoniae, C. pneumoniae, L. pneumophila* Sg1, and human DNA (A), and a no template control reaction (B).

Any nucleic acid and amino acid sequences listed herein or in the accompanying sequence listing are shown using standard letter abbreviations for nucleotide bases, and three letter code for amino acids, as defined in 37 C.F.R. §1.822. In at least some cases, only one strand of each nucleic acid sequence is shown, but the complementary strand is understood as included by any reference to the displayed strand.

The Sequence_Listing is submitted as an ASCII text file in the form of the file named Sequence_Listing.txt, which was created on Oct. 8, 2012, and is 13,355 bytes, which is incorporated by reference herein.

In the provided sequences:
SEQ ID NO: 1 is an exemplary nucleotide sequence of *Mycoplasma pneumoniae* CARDS toxin.
SEQ ID NO: 2 is an exemplary nucleotide sequence of *Chlamydophila pneumoniae* ArgR.

SEQ ID NO: 3 is an exemplary nucleotide sequence of *Legionella pneumophila* SsrA.
SEQ ID NO: 4 is an exemplary nucleotide sequence of human RNase P.
SEQ ID NO: 5 is the nucleotide sequence of a *M. pneumoniae* CARDS toxin forward real-time PCR primer.
SEQ ID NO: 6 is the nucleotide sequence of a *M. pneumoniae* CARDS toxin reverse real-time PCR primer.
SEQ ID NO: 7 is the nucleotide sequence of a *M. pneumoniae* CARDS toxin real-time PCR probe.
SEQ ID NO: 8 is the nucleotide sequence of a *C. pneumoniae* ArgR forward real-time PCR primer.
SEQ ID NO: 9 is the nucleotide sequence of a *C. pneumoniae* ArgR reverse real-time PCR primer.
SEQ ID NO: 10 is the nucleotide sequence of a *C. pneumoniae* ArgR real-time PCR probe.
SEQ ID NO: 11 is the nucleotide sequence of a *Legionella* SsrA forward real-time PCR primer.
SEQ ID NO: 12 is the nucleotide sequence of a *Legionella* SsrA reverse real-time PCR primer.
SEQ ID NO: 13 is the nucleotide sequence of a *Legionella* SsrA real-time PCR probe.
SEQ ID NO: 14 is the nucleotide sequence of a human RNase P forward real-time PCR primer.
SEQ ID NO: 15 is the nucleotide sequence of a human RNase P reverse real-time PCR primer.
SEQ ID NO: 16 is the nucleotide sequence of a human RNase P real-time PCR probe.
SEQ ID NO: 17 is the nucleotide sequence of an exemplary *Legionella* SsrA probe for use with a minor groove binder (MGB).
SEQ ID NO: 18 is the nucleotide sequence of an exemplary *M. pneumoniae* orf521.
SEQ ID NO: 19 is the nucleotide sequence of a *M. pneumoniae* orf521 forward real-time PCR primer.
SEQ ID NO: 20 is the nucleotide sequence of a *M. pneumoniae* orf521 reverse real-time PCR primer.
SEQ ID NO: 21 is the nucleotide sequence of a *M. pneumoniae* orf521 real-time PCR probe.

DETAILED DESCRIPTION

Although *M. pneumoniae, C. pneumoniae* and *Legionella* spp. have long been established as key causative agents for atypical bacterial CAP infections, rapid and reliable diagnosis continues to be a challenge. The multiplex real-time PCR assay described here offers an effective tool for rapid and simultaneous detection of three leading causes of atypical bacterial pneumonia. Real-time PCR methods and probes and primers for such methods are disclosed herein.

In some embodiments, the disclosed methods utilize the CARDS toxin gene to detect *M. pneumoniae*, the ArgR gene to detect *C. pneumoniae*, the SsrA gene to detect *Legionella* spp. (including, but not limited to, *L. pneumophila, L. micdadei, L. bozemanii*, and *L. longbeachae*), and human RNase P as an internal positive control, enabling a complete single-tube test. Further, in some embodiments the disclosed methods utilize probes labeled with combinations of donor and acceptor/quencher fluorophores that allow the multiplex detection of four target nucleic acids from different organisms in a single reaction.

In particular, the multiplex assay provides numerous advantages over existing detection methodologies. A significant improvement in specimen throughput is realized, since all three agents can be tested in a single tube, along with a control. This results in faster turnaround time from specimen receipt to result, a feature that may be especially important during respiratory outbreaks in which the initial etiology is unknown. Additionally, the potential for error is decreased in both PCR master mix preparation and sample addition to the reaction well, since only one master mix is required and the specimen extract can be tested in a single reaction well. This also allows for conservation of the specimen extract and thus affords greater flexibility and opportunity for follow-up or additional testing. A further advantage is that since less specimen volume is required to perform this assay, the extraction procedure may be modified to decrease elution volume, thereby concentrating the extract to further increase sensitivity.

I. ABBREVIATIONS

BAL: bronchoalveolar lavage
CAP: community acquired pneumonia
CARDS toxin: community acquired respiratory distress syndrome toxin
NP: nasopharyngeal
OP: oropharyngeal
RNase P: ribonuclease P

II. TERMS

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. As used herein, "comprises" means "includes." Thus, "comprising A or B," means "including A, B, or A and B," without excluding additional elements. It is further to be understood that all base sizes or amino acid sizes, and all molecular weight or molecular mass values, given for nucleic acids or polypeptides are approximate, and are provided for description. All publications, patent applications, patents, and other references mentioned herein are incorporated by reference in their entirety for all purposes. All GenBank Accession Nos. mentioned herein are incorporated by reference in their entirety as present on Apr. 16, 2010.

Although methods and materials similar or equivalent to those described herein can be used in the practice or testing of the present disclosure, suitable methods and materials are described below. In case of conflict, the present specification, including explanations of terms, will control. In addition, the materials, methods, and examples are illustrative only and not intended to be limiting.

In order to facilitate review of the various embodiments of the invention, the following explanations of specific terms are provided:

Amplification: To increase the number of copies of a nucleic acid molecule. The resulting amplification products are called "amplicons." Amplification of a nucleic acid molecule (such as a DNA or RNA molecule) refers to use of a technique that increases the number of copies of a nucleic acid molecule in a sample, such as a *M. pneumoniae* CARDS toxin nucleic acid (for example, SEQ ID NO: 1), a *C. pneumoniae* ArgR nucleic acid (for example, SEQ ID NO: 2), a *Legionella* SsrA nucleic acid (for example, SEQ ID NO: 3), and/or a human RNase P nucleic acid (for example, SEQ ID NO: 4). An example of amplification is the polymerase chain reaction (PCR), in which a sample is contacted with a pair of oligonucleotide primers under conditions that allow for the hybridization of the primers to a nucleic acid template in the sample. The primers are extended under suitable conditions, dissociated from the template, re-annealed, extended, and dissociated to amplify the number of copies of the nucleic acid. This cycle can be repeated. The product of amplification can be characterized by such techniques as electrophoresis, restriction endonuclease cleavage patterns, oligonucleotide hybridization or ligation, and/or nucleic acid sequencing.

Other examples of in vitro amplification techniques include real-time PCR; quantitative real-time PCR; reverse transcriptase PCR (RT-PCR); real-time reverse transcriptase PCR (rt RT-PCR); nested PCR; strand displacement amplification (see U.S. Pat. No. 5,744,311); transcription-free isothermal amplification (see U.S. Pat. No. 6,033,881); repair chain reaction amplification (see WO 90/01069); ligase chain reaction amplification (see European patent publication EP-A-320 308); gap filling ligase chain reaction amplification (see U.S. Pat. No. 5,427,930); coupled ligase detection and PCR (see U.S. Pat. No. 6,027,889); and NASBA™ RNA transcription-free amplification (see U.S. Pat. No. 6,025,134), amongst others.

*Chlamydophila pneumoniae* (*Chlamydia pneumoniae*): A bacterium that causes pneumonia in humans. *C. pneumoniae* is responsible for about 10% of atypical community acquired pneumonia. Multiple strains of *C. pneumoniae* have been identified, such as TW-183, AR39, CWL029, J138, and LPCoLN. Nucleic acid and protein sequences for *C. pneumoniae* are publicly available. For example, GenBank Accession Nos. NC_002179, NC_000922, NC_002491, and NC_005043 provide exemplary *C. pneumoniae* genome sequences.

The *C. pneumoniae* arginine repressor (ArgR) is a molecule that modulates transcription of arginine transport-related genes in response to intracellular arginine levels in *C. pneumoniae*. An exemplary *C. pneumoniae* nucleotide sequence of ArgR is found at GenBank Accession No. NC_005043 (complement 230090 . . . 230533) (SEQ ID NO: 2). GenBank Accession Nos. NC_002179 (608163 . . . 608606), AE001363 (complement, 232683 . . . 233126), and NC_002491 (complement, 232298 . . . 232741) provide additional exemplary *C. pneumoniae* ArgR nucleic acid sequences.

Consists essentially of/Consists of: With regard to a polynucleotide (such as a probe or primer), a polynucleotide consists essentially of a specified nucleotide sequence if it does not include any additional nucleotides. However, the polynucleotide can include additional non-nucleic acid components, such as labels (for example, fluorescent, radioactive, or solid particle labels), sugars or lipids. With regard to a polynucleotide, a polynucleotide that consists of a specified nucleotide sequence does not include any additional nucleotides, nor does it include additional non-nucleic acid components, such as lipids, sugars or labels.

Detect: To determine if an agent (such as a signal, particular nucleotide, amino acid, nucleic acid molecule, and/or organism) is present or absent, for example *M. pneumoniae, C. pneumoniae*, and/or *Legionella* spp. (for example, a *M. pneumoniae* nucleic acid, a *C. pneumoniae* nucleic acid and/ or a *Legionella* spp. nucleic acid). In some examples, this can further include quantification. For example, use of the disclosed probes in particular examples permits detection of a fluorophore, for example, detection of a signal from a fluorophore, which can be used to determine if a nucleic acid corresponding to a *M. pneumoniae* nucleic acid (such as a *M. pneumoniae* CARDS toxin nucleic acid molecule), a *C. pneumoniae* nucleic acid (such as a *C. pneumoniae* ArgR nucleic acid molecule), or a *Legionella* spp. nucleic acid (such as a *Legionella* SsrA nucleic acid molecule) is present. The detection of a nucleic acid molecule of the particular bacteria (such as *M. pneumoniae*, *C. pneumoniae*, and/or *Legionella* spp.) indicates the presence of the bacteria in the sample, for example a *M. pneumoniae*, *C. pneumoniae*, or *Legionella* spp. infection in the sample.

Emission or emission signal: The light of a particular wavelength generated from a source. In particular examples, an emission signal is emitted from a fluorophore after the fluorophore absorbs light at its excitation wavelength(s).

Excitation or excitation signal: The light of a particular wavelength necessary and/or sufficient to excite an electron transition to a higher energy level. In particular examples, an excitation signal is the light of a particular wavelength necessary and/or sufficient to excite a fluorophore to a state such that the fluorophore will emit a different (such as a longer) wavelength of light than the wavelength of light from the excitation signal.

Fluorophore: A chemical compound, which when excited by exposure to a particular stimulus, such as a defined wavelength of light, emits light (fluoresces), for example at a different wavelength (such as a longer wavelength of light).

Fluorophores are part of the larger class of luminescent compounds. Luminescent compounds include chemiluminescent molecules, which do not require a particular wavelength of light to luminesce, but rather use a chemical source of energy. Therefore, the use of chemiluminescent molecules (such as aequorin) eliminates the need for an external source of electromagnetic radiation, such as a laser.

Examples of particular fluorophores that can be used in the *M. pneumoniae*, *C. pneumoniae*, *Legionella* spp., and human-specific probes and primers disclosed herein are known to those of skill in the art and include those provided in U.S. Pat. No. 5,866,366 to Nazarenko et al., such as 4-acetamido-4'-isothiocyanatostilbene-2,2'disulfonic acid; acridine and derivatives such as acridine and acridine isothiocyanate, 5-(2'-aminoethyl)aminonaphthalene-1-sulfonic acid (EDANS), 4-amino-N-[3-vinylsulfonyl)phenyl]naphthalimide-3,5 disulfonate (Lucifer Yellow VS), N-(4-anilino-1-naphthyl)maleimide, anthranilamide; Brilliant Yellow; coumarin and derivatives such as coumarin, 7-amino-4-methylcoumarin (AMC, Coumarin 120), 7-amino-4-trifluoromethylcouluarin (Coumaran 151); cyanosine; 4',6-diaminidino-2-phenylindole (DAPI); 5',5"-dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino] naphthalene-1-sulfonyl chloride (DNS, dansyl chloride); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6-dichlorotriazin-2-yl)aminofluorescein (DTAF), 2'7'-dimethoxy-4'5'-dichloro-6-carboxyfluorescein (JOE), fluorescein, fluorescein isothiocyanate (FITC), QFITC (XRITC), 6-carboxyfluorescein (HEX), and TET (tetramethyl fluorescein); fluorescamine; IR144; IR1446; Malachite Green isothiocyanate; 4-methylumbelliferone; ortho-cresolphthalein; nitrotyrosine; pararosaniline; Phenol Red; B-phycoerythrin; o-phthaldialdehyde; pyrene and derivatives such as pyrene, pyrene butyrate, and succinimidyl 1-pyrene butyrate; Reactive Red 4 (CIBACRON™ Brilliant Red 3B-A); rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, N,N,N',N'-tetramethyl-6-carboxyrhodamine (TAMRA), tetramethyl rhodamine, and tetramethyl rhodamine isothiocyanate (TRITC); sulforhodamine B; sulforhodamine 101 and sulfonyl chloride derivative of sulforhodamine 101 (Texas Red); riboflavin; rosolic acid and terbium chelate derivatives; LightCycler Red 640; Cy5.5; and Cy56-carboxyfluorescein; boron dipyrromethene difluoride (BODIPY); acridine; stilbene; Cy3; Cy5, VIC® (Applied Biosystems); LC Red 640; LC Red 705; and Yakima yellow amongst others. Additional examples of fluorophores include Quasar® 670, Quasar® 570, CAL Fluor® Red 590, CAL Fluor® Red 610, CAL Fluor® 615, CAL Fluor® Red 635, CAL Fluor® Green 520, CAL Fluor® Gold 540, and CAL Fluor® Orange 560 (Biosearch Technologies, Novato, Calif.).

Other suitable fluorophores include those known to those skilled in the art, for example those available from Molecular Probes/Life Technologies (Carlsbad, Calif.). In particular examples, a fluorophore is used as a donor fluorophore or as an acceptor fluorophore.

"Acceptor fluorophores" are fluorophores which absorb energy from a donor fluorophore, for example in the range of about 400 to 900 nm (such as in the range of about 500 to 800 nm). Acceptor fluorophores generally absorb light at a wavelength which is usually at least 10 nm higher (such as at least 20 nm higher) than the maximum absorbance wavelength of the donor fluorophore, and have a fluorescence emission maximum at a wavelength ranging from about 400 to 900 nm. Acceptor fluorophores have an excitation spectrum that overlaps with the emission of the donor fluorophore, such that energy emitted by the donor can excite the acceptor. Ideally, an acceptor fluorophore is capable of being attached to a nucleic acid molecule.

In a particular example, an acceptor fluorophore is a dark quencher, such as Dabcyl, QSY7 (Molecular Probes), QSY33 (Molecular Probes), BLACK HOLE QUENCHERS™ (Biosearch Technologies; such as BHQ0, BHQ1, BHQ2, and BHQ3), ECLIPSE™ Dark Quencher (Epoch Biosciences), or IOWA BLACK™ (Integrated DNA Technologies). A quencher can reduce or quench the emission of a donor fluorophore. In such an example, instead of detecting an increase in emission signal from the acceptor fluorophore when in sufficient proximity to the donor fluorophore (or detecting a decrease in emission signal from the acceptor fluorophore when a significant distance from the donor fluorophore), an increase in the emission signal from the donor fluorophore can be detected when the quencher is a significant distance from the donor fluorophore (or a decrease in emission signal from the donor fluorophore when in sufficient proximity to the quencher acceptor fluorophore).

"Donor Fluorophores" are fluorophores or luminescent molecules capable of transferring energy to an acceptor fluorophore, thereby generating a detectable fluorescent signal from the acceptor. Donor fluorophores are generally compounds that absorb in the range of about 300 to 900 nm, for example about 350 to 800 nm. Donor fluorophores have a strong molar absorbance coefficient at the desired excitation wavelength, for example greater than about $10^3$ $M^{-1}$ $cm^{-1}$.

Fluorescence Resonance Energy Transfer (FRET): A spectroscopic process by which energy is passed between an initially excited donor to an acceptor molecule separated by 10-100 Å. The donor molecules typically emit at shorter wavelengths that overlap with the absorption of the acceptor molecule. The efficiency of energy transfer is proportional to the inverse sixth power of the distance (R) between the donor and acceptor ($1/R^6$) fluorophores and occurs without emission of a photon. In applications using FRET, the donor and acceptor dyes are different, in which case FRET can be detected either by the appearance of sensitized fluorescence of the acceptor or by quenching of donor fluorescence. For example, if the donor's fluorescence is quenched it indicates the donor and acceptor molecules are within the Forster radius (the distance where FRET has 50% efficiency, about 20-60 Å), whereas if the donor fluoresces at its characteristic wavelength, it denotes that the distance between the donor and acceptor molecules has increased beyond the Forster radius, such as when a TAQMAN® probe is degraded by Taq polymerase following hybridization of the probe to a target nucleic acid sequence or when a hairpin probe is hybridized to a target nucleic acid sequence. In another example, energy is transferred via FRET between two different fluorophores such that the acceptor molecule can emit light at its characteristic wavelength, which is always longer than the emission wavelength of the donor molecule.

Examples of oligonucleotides using FRET that can be used to detect amplicons include linear oligoprobes, such as Hyb-Probes, 5' nuclease oligoprobes, such as TAQMAN® probes, hairpin oligoprobes, such as molecular beacons, scorpion primers and UniPrimers, minor groove binding probes, and self-fluorescing amplicons, such as sunrise primers or LUX primers.

Hybridization: The ability of complementary single-stranded DNA or RNA to form a duplex molecule (also referred to as a hybridization complex). Nucleic acid hybridization techniques can be used to form hybridization complexes between a probe or primer and a nucleic acid, such as a *M. pneumoniae* CARDS toxin nucleic acid molecule, a *C. pneumoniae* ArgR nucleic acid molecule, a *Legionella* SsrA nucleic acid molecule, and/or a human RNase P nucleic acid molecule. For example, a probe or primer (such as any of SEQ ID NOs: 5-16) having some homology to a disclosed *M. pneumoniae, C. pneumoniae, Legionella*, or human nucleic acid molecule will form a hybridization complex with a complementary nucleic acid molecule (such as any of SEQ ID NOs: 1-4).

Hybridization conditions resulting in particular degrees of stringency will vary depending upon the nature of the hybridization method and the composition and length of the hybridizing nucleic acid sequences. Generally, the temperature of hybridization and the ionic strength (such as the $Na^+$ concentration) of the hybridization buffer will determine the stringency of hybridization. Calculations regarding hybridization conditions for attaining particular degrees of stringency are discussed in Sambrook et al., (1989) *Molecular Cloning*, second edition, Cold Spring Harbor Laboratory, Plainview, N.Y. (chapters 9 and 11). The following is an exemplary set of hybridization conditions and is not limiting:

Very High Stringency (Detects Sequences that Share at Least 90% Identity)
Hybridization: 5×SSC at 65° C. for 16 hours
Wash twice: 2×SSC at room temperature (RT) for 15 minutes each
Wash twice: 0.5×SSC at 65° C. for 20 minutes each High Stringency (Detects Sequences that Share at Least 80% Identity)
Hybridization: 5×-6×SSC at 65° C.-70° C. for 16-20 hours
Wash twice: 2×SSC at RT for 5-20 minutes each
Wash twice: 1×SSC at 55° C.-70° C. for 30 minutes each Low Stringency (Detects Sequences that Share at Least 50% Identity)
Hybridization: 6×SSC at RT to 55° C. for 16-20 hours
Wash at least twice: 2×-3×SSC at RT to 55° C. for 20-30 minutes each The probes and primers disclosed herein can hybridize to nucleic acid molecules under low stringency, high stringency, and very high stringency conditions.

Label (Detectable label): An agent capable of detection, for example by spectrophotometry, flow cytometry, or microscopy. For example, a label can be attached to a nucleotide, thereby permitting detection of the nucleotide, such as detection of the nucleic acid molecule of which the nucleotide is a part, such as a probe and/or primer. Examples of labels include, but are not limited to, radioactive isotopes, enzyme substrates, co-factors, ligands, chemiluminescent agents, fluorophores, haptens, enzymes, and combinations thereof. Methods for labeling and guidance in the choice of labels appropriate for various purposes are discussed for example in Sambrook et al. (*Molecular Cloning: A Laboratory Manual*, Cold Spring Harbor, N.Y., 1989) and Ausubel et al. (In *Current Protocols in Molecular Biology*, John Wiley & Sons, New York, 1998).

*Legionella*: A genus of gram-negative bacteria that cause Legionellosis, including pneumonia. *L. pneumophila* Sg1 is most common, causing about 70% of cases of Legionellosis. *L. pneumophila* Sg2, Sg4, and Sg6, as well as *L. bozemanii, L. longbeachae*, and *L. micdadei* also have been reported as causing disease. Additional *Legionella* species include those listed in Fields et al., *Clin. Microbiol. Rev.* 15:506-526, 2002. Nucleic acid and protein sequences for *Legionella* spp. are publicly available. For example, GenBank Accession Nos. NC_009494, NC_006369, NC_006368, and NC_002942 provide exemplary *L. pneumophila* genome sequences.

The *Legionella* SsrA gene (also known as 10Sa RNA or tmRNA) is an RNA with tRNA-like and mRNA-like properties that mediates tagging for degradation of a protein product of a ribosome that reaches the end of an mRNA without encountering a stop codon (Williams and Bartel, *RNA* 2:1306-1310, 1996). An exemplary *Legionella pneumophila* nucleotide sequence of SsrA is found at GenBank Accession No. U68079 (SEQ ID NO: 3). GenBank Accession Nos. AE017354 (172934-173295), CP628337 (175142-175503), CR628336 (182399-182760), CP000675 (181371-181732), and FN650140 (complement, 3822176-3821816) provide additional exemplary *Legionella* SsrA nucleic acid sequences.

Multiplex PCR: Amplification of multiple nucleic acid species in a single PCR reaction, such as a single real-time PCR reaction. By multiplexing, target nucleic acids (including an endogenous control, in some examples) can be amplified in single tube. In some examples, multiplex PCR permits the simultaneous detection of the amplification products of *M. pneumoniae* (such as *M. pneumoniae* CARDS toxin), *C. pneumoniae* (such as *C. pneumoniae* ArgR), and *Legionella* (such as *Legionella* SsrA) nucleic acids using the disclosed probes or even another nucleic acid, such as a control nucleic acid, for example a human RNase P nucleic acid.

*Mycoplasma pneumoniae*: A bacterium that causes pneumonia in humans. *M. pneumoniae* is responsible for about 15-20% of atypical community acquired pneumonia. Multiple strains of *M. pneumoniae* have been identified, such as M129 and FH. Nucleic acid and protein sequences for *M. pneumoniae* are publicly available. For example, GenBank Accession No. NC_000912 provides an exemplary *M. pneumoniae* genome sequence.

The *M. pneumoniae* CARDS toxin (community acquired respiratory distress syndrome toxin) is an ADP-ribosyltransferase that has been identified as a potential virulence factor in *M. pneumoniae* (Kannan and Baseman, *Proc. Natl. Acad. Sci. USA* 103:6724-6729, 2006). An exemplary *M. pneumoniae* nucleotide sequence of CARDS toxin is found at GenBank Accession No. DQ447750 (SEQ ID NO: 1). GenBank Accession Nos. DQ447746, DQ447747, DQ447748, and DQ447749 provide further exemplary *M. pneumoniae* CARDS toxin nucleic acid sequences.

An exemplary nucleotide sequence of orf521 of *M. pneumoniae* is found at nucleotides 10624-12189 of GenBank Accession No. U43738 and is provided herein as SEQ ID NO: 18. GenBank Accession No. CP002077 (nucleotides 709107-710672, reverse complement) provides an additional exemplary *M. pneumoniae* orf521 nucleic acid sequence.

Nucleic acid (molecule or sequence): A deoxyribonucleotide or ribonucleotide polymer including without limitation, cDNA, mRNA, genomic DNA, and synthetic (such as chemically synthesized) DNA or RNA. The nucleic acid can be double stranded or single stranded. Where single stranded, the nucleic acid can be the sense strand or the antisense strand. Nucleic acids can include natural nucleotides (such as A, T/U, C, and G), and can include analogs of natural nucleotides, such as labeled nucleotides. In some examples, a nucleic acid is a *M. pneumoniae* nucleic acid, a *C. pneumoniae* nucleic acid, a *Legionella* spp. nucleic acid, and/or a human nucleic acid, which can include nucleic acids purified from *M. pneumoniae, C. pneumoniae, Legionella* spp., or human, as well as the amplification products of such nucleic acids.

Nucleic acid molecules can be modified chemically or biochemically or can contain non-natural or derivatized nucleotide bases, as will be readily appreciated by those of skill in the art. Such modifications include, for example, labels, methylation, substitution of one or more of the naturally occurring nucleotides with an analog, internucleotide modifications, such as uncharged linkages (for example, methyl phosphonates, phosphotriesters, phosphoramidates, or carbamates), charged linkages (for example, phosphorothioates, or phosphorodithioates), pendent moieties (for example, peptides), intercalators (for example, acridine, psoralen, and others), chelators, alkylators, and modified linkages (for example, alpha anomeric nucleic acids). The term "nucleic acid molecule" also includes any topological conformation, including single-stranded, double-stranded, partially duplexed, triplexed, hairpinned, circular and padlocked conformations.

Primers: Short nucleic acid molecules, for instance DNA oligonucleotides 10-100 nucleotides in length, such as about 10, 15, 20, 25, 30, 40, 45, or 50 nucleotides or more in length. Primers can be annealed to a complementary target DNA strand by nucleic acid hybridization to form a hybrid between the primer and the target DNA strand. A primer can be extended along the target nucleic acid molecule by a polymerase enzyme. Therefore, primers can be used to amplify a target nucleic acid molecule, wherein the sequence of the primer is specific for the target nucleic acid molecule, for example so that the primer will hybridize to the target nucleic acid molecule under very high stringency hybridization conditions.

Primer pairs can be used for amplification of a nucleic acid sequence, for example, by PCR, real-time PCR, or other nucleic-acid amplification methods known in the art. An "upstream" or "forward" primer is a primer 5' to a reference point on a nucleic acid sequence. A "downstream" or "reverse" primer is a primer 3' to a reference point on a nucleic acid sequence.

In particular examples, a primer is at least 10 nucleotides in length, such as at least 10 contiguous nucleotides complementary to a target nucleic acid molecule. Particular lengths of primers that can be used to practice the methods of the present disclosure include primers having at least 10, such as at least 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more contiguous nucleotides complementary to the target nucleic acid molecule to be amplified, such as a primer of 10-60 nucleotides, 15-50 nucleotides, 20-40 nucleotides, 25-50, nucleotides, or 10-40 nucleotides.

Methods for preparing and using nucleic acid primers are described, for example, in Sambrook et al. (In *Molecular Cloning: A Laboratory Manual*, CSHL, New York, 1989), Ausubel et al. (ed.) (In *Current Protocols in Molecular Biology*, John Wiley & Sons, New York, 1998), and Innis et al. (*PCR Protocols, A Guide to Methods and Applications*, Academic Press, Inc., San Diego, Calif., 1990). PCR primer pairs can be derived from a known sequence, for example, by using computer programs intended for that purpose such as Primer (Version 0.5, 1991, Whitehead Institute for Biomedical Research, Cambridge, Mass.). One of ordinary skill in the art will appreciate that the specificity of a particular primer increases with its length. Thus, in order to obtain greater specificity, primers can be selected that include at least 10, at least 15, at least 20, at least 25, at least 30, at least 35, at least 40, at least 45, at least 50 or more consecutive nucleotides of a target sequence.

Probe: A short sequence of nucleotides, such as at least 8, at least 10, at least 15, at least 20, at least 25, or at least 30 nucleotides in length, used to detect the presence of a complementary sequence by molecular hybridization. In particular examples, probes include a label that permits detection of probe:target sequence hybridization complexes. Typical labels include radioactive isotopes, enzyme substrates, co-factors, ligands, chemiluminescent or fluorescent agents, haptens, and enzymes. Methods for labeling and guidance in the choice of labels appropriate for various purposes are discussed, for example, in Sambrook et al., *Molecular Cloning: A Laboratory Manual*, Cold Spring Harbor Laboratory Press (1989) and Ausubel et al., *Current Protocols in Molecular Biology*, Greene Publishing Associates and Wiley-Intersciences (1987).

In a particular example, a probe includes at least one fluorophore, such as an acceptor fluorophore or donor fluorophore. For example, a fluorophore can be attached at the 5'- or 3'-end of the probe. In specific examples, the fluorophore is attached to the base at the 5'-end of the probe, the base at its 3'-end, the phosphate group at its 5'-end or a modified base, such as a T internal to the probe.

Probes are generally at least 10 nucleotides in length, such as at least 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 51, 52, 53, 54, 55, 56, 57, 58, 59, 60, or more contiguous nucleotides complementary to the target nucleic acid molecule, such as 10-60 nucleotides, 30-60 nucleotides, 20-50 nucleotides, 30-50 nucleotides, 20-40 nucleotides, or 10-40 nucleotides.

Quenching of fluorescence: A reduction of fluorescence. For example, quenching of a fluorophore's fluorescence occurs when a quencher molecule (such as the fluorescence quenchers listed above) is present in sufficient proximity to the fluorophore that it reduces the fluorescence signal (for example, prior to the binding of a probe to a nucleic acid sequence, when the probe contains a fluorophore and a quencher).

Real-time PCR: A method for detecting and measuring products generated during each cycle of a PCR, which are proportionate to the amount of template nucleic acid prior to the start of PCR. The information obtained, such as an amplification curve, can be used to determine the presence of a target nucleic acid (such as a *M. pneumoniae, C. pneumoniae,* or *Legionella* spp. nucleic acid) and/or quantitate the initial amounts of a target nucleic acid sequence. Exemplary procedures for real-time PCR can be found in "Quantitation of DNA/RNA Using Real-Time PCR Detection" published by Perkin Elmer Applied Biosystems (1999); *PCR Protocols* (Academic Press, New York, 1989); and *A-Z of Quantitative PCR*, Bustin (ed.), International University Line, La Jolla, Calif., 2004.

In some examples, the amount of amplified target nucleic acid (for example a *M. pneumoniae* CARDS toxin nucleic acid molecule, a *C. pneumoniae* ArgR nucleic acid, a *Legionella* spp. SsrA nucleic acid, and/or a human RNase P nucleic acid) is detected using a labeled probe, such as a probe labeled with a fluorophore, for example a TAQMAN® probe. In this example, the increase in fluorescence emission is measured in real-time, during the course of the real-time PCR. This increase in fluorescence emission is directly related to the increase in target nucleic acid amplification. In some examples, the change in fluorescence (dRn) is calculated using the equation $dRn=Rn^+ - Rn^-$, with $Rn^+$ being the fluorescence emission of the product at each time point and $Rn^-$ being the fluorescence emission of the baseline. The dRn values are plotted against cycle number, resulting in amplification plots for each sample. The threshold value ($C_t$) is the PCR cycle number at which the fluorescence emission (dRn) exceeds a chosen threshold, which is typically 10 times the standard deviation of the baseline (this threshold level can, however, be changed if desired).

The threshold cycle is when the system begins to detect the increase in the signal associated with an exponential growth of PCR product during the log-linear phase. This phase provides information about the reaction. The slope of the log-linear phase is a reflection of the amplification efficiency. The efficiency of the reaction can be calculated by the following equation: $E=10^{(-1/slope)}$. The efficiency of the PCR should be 90-100% meaning doubling of the amplicon at each cycle. This corresponds to a slope of −3.1 to −3.6 in the $C_t$ vs. log-template amount standard curve. In order to obtain accurate and reproducible results, reactions should have efficiency as close to 100% as possible (meaning a two-fold increase of amplicon at each cycle).

Ribonuclease P (RNase P): The human ribonuclease P gene is utilized as an amplification control in the disclosed real-time PCR assays, and also to monitor nucleic acid extraction efficiency. An exemplary human nucleotide sequence of RNase P 30 kDa subunit (RPP30) is found at GenBank Accession No. NM_006413 (SEQ ID NO: 4). GenBank Accession Nos. NM_001098016 and BC006991 provide further exemplary human RNase P nucleic acid sequences.

Sample: As used herein, a sample (for example a biological sample) includes all clinical samples useful for detecting CAP infection (such as *M. pneumoniae, C. pneumoniae,* and/or *Legionella* spp. infection) in subjects, including, but not limited to, cells, tissues, and bodily fluids, such as: blood; derivatives and fractions of blood, such as serum; extracted galls; biopsied or surgically removed tissue, including tissues that are, for example, unfixed, frozen, fixed in formalin and/or embedded in paraffin; autopsy material; tears; milk; skin scrapes; surface washings; urine; sputum; cerebrospinal fluid; prostate fluid; pus; bone marrow aspirates; middle ear fluids; bronchoalveolar lavage; tracheal aspirates; nasopharyngeal aspirates; oropharyngeal aspirates; or saliva. A sample may also include environmental samples, for example, food, water (such as water from cooling towers, swimming pools, domestic water systems, fountains, or freshwater creeks or ponds), or other materials that may contain or be contaminated with a pathogen. In particular embodiments, the biological sample is obtained from an animal subject, such as in the form of middle ear fluids, bronchoalveolar lavage, tracheal aspirates, sputum, nasopharyngeal aspirates or swabs, oropharyngeal aspirates or swabs, or saliva.

Sequence identity/similarity: The identity/similarity between two or more nucleic acid sequences, or two or more amino acid sequences, is expressed in terms of the identity or similarity between the sequences. Sequence identity can be measured in terms of percentage identity; the higher the percentage, the more identical the sequences are. Homologs or orthologs of nucleic acid or amino acid sequences possess a relatively high degree of sequence identity/similarity when aligned using standard methods.

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene*, 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215:403-10, 1990, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biological Information (NCBI, National Library of Medicine, Building 38A, Room 8N805, Bethesda, Md. 20894) and on the Internet, for use in connection with the sequence analysis programs blastp, blastn, blastx, tblastn, and tblastx. Blastn is used to compare nucleic acid sequences, while blastp is used to compare amino acid sequences. Additional information can be found at the NCBI web site.

Once aligned, the number of matches is determined by counting the number of positions where an identical nucleotide or amino acid residue is present in both sequences. The percent sequence identity is determined by dividing the number of matches either by the length of the sequence set forth in the identified sequence, or by an articulated length (such as 100 consecutive nucleotides or amino acid residues from a sequence set forth in an identified sequence), followed by multiplying the resulting value by 100.

One indication that two nucleic acid molecules are closely related is that the two molecules hybridize to each other under stringent conditions. Stringent conditions are sequence-dependent and are different under different environmental parameters.

The nucleic acid probes and primers disclosed herein are not limited to the exact sequences shown, as those skilled in the art will appreciate that changes can be made to a sequence, and not substantially affect the ability of the probe or primer to function as desired. For example, sequences having at least 80%, at least 85%, at least 90%, at least 91%, at least 92%, at least 93%, at least 94%, at least 95%, at least 96%, at least 97%, at least 98%, or at least 99%, such as 100% sequence identity to any of SEQ ID NOs: 5-16 are provided herein. One of skill in the art will appreciate that these sequence identity ranges are provided for guidance only; it is possible that probes and primer can be used that fall outside these ranges.

Signal: A detectable change or impulse in a physical property that provides information. In the context of the disclosed methods, examples include electromagnetic signals such as light, for example light of a particular quantity or wavelength. In certain examples, the signal is the disappearance of a physical event, such as quenching of light.

Sensitivity and specificity: Statistical measurements of the performance of a binary classification test. Sensitivity measures the proportion of actual positives which are correctly identified (e.g., the percentage of samples that are identified as including nucleic acid from a particular organism). Specificity measures the proportion of negatives which are correctly identified (e.g., the percentage of samples that are identified as not including nucleic acid from a particular organism).

Subject: A living multi-cellular vertebrate organism, a category that includes human and non-human mammals.

Target nucleic acid molecule: A nucleic acid molecule whose detection, quantitation, qualitative detection, or a combination thereof, is intended. The nucleic acid molecule need not be in a purified form. Various other nucleic acid molecules can also be present with the target nucleic acid molecule. For example, the target nucleic acid molecule can be a specific nucleic acid molecule (which can include RNA or DNA), the amplification of which is intended. In some examples, a target nucleic acid includes a *M. pneumoniae* CARDS toxin nucleic acid, a *C. pneumoniae* ArgR nucleic acid, a *Legionella* SsrA nucleic acid, or a human RNase P nucleic acid. Purification or isolation of the target nucleic acid molecule, if needed, can be conducted by methods known to those in the art, such as by using a commercially available purification kit or the like.

III. METHODS FOR DETECTION OF CAP PATHOGENS

Methods for detecting the presence of a pathogen such as *M. pneumoniae, C. pneumoniae*, and/or *Legionella* spp. in a sample are disclosed, for example, utilizing the primers and probes disclosed herein.

The methods described herein may be used for any purpose for which detection of *M. pneumoniae, C. pneumoniae*, and/or *Legionella* spp. (including, but not limited to, *L. pneumophila, L. bozemanii, L. longbeachae*, or *L. micdadei*) is desirable, including diagnostic and prognostic applications, such as in laboratory and clinical settings. Appropriate samples include any conventional environmental or biological samples, including clinical samples obtained from a human or veterinary subject. Suitable samples include all biological samples useful for detection of bacterial infection in subjects, including, but not limited to, cells, tissues (for example, lung, liver, and kidney), autopsy samples, bone marrow aspirates, bodily fluids (for example, blood, serum, urine, cerebrospinal fluid, middle ear fluids, bronchoalveolar lavage, tracheal aspirates, sputum, nasopharyngeal aspirates, oropharyngeal aspirates, or saliva), eye swabs, cervical swabs, vaginal swabs, rectal swabs, stool, and stool suspensions. Standard techniques for acquisition of such samples are available. See for example, Schluger et al., *J. Exp. Med.* 176:1327-1333, 1992; Bigby et al., *Am. Rev. Respir. Dis.* 133:515-518, 1986; Kovacs et al., *N. Engl. J. Med.* 318:589-593, 1988; and Ognibene et al., *Am. Rev. Respir. Dis.* 129:929-932, 1984.

In some embodiments, the nucleic acids detected using the methods provided herein include nucleic acid molecules from *M. pneumoniae, C. pneumoniae*, or *Legionella* spp. In some examples, *M. pneumoniae* includes, but is not limited to, *M. pneumoniae* strains such as M129, FH, PI-1428, B176, and MAC. In additional examples, *C. pneumoniae* includes, but is not limited to, *C. pneumoniae* strains such as AR-388, BR-393, W6, IOL-207, FML-7, FML-12, FML-16, FML-19, K66, TW-183, CM1, CWL-029, TW-2043, TW-2023, CWL-011, CDL-050, BAL-16. In further examples, *Legionella* includes, but is not limited to, *L. pneumophila* (such as *L. pneumophila* subtypes Sg1, Sg2, Sg4, and Sg6), *L. bozemanii, L. longbeachae, L. micdadei, L. binninghamensis, D. dumoffi, L. hackliae, L. maceachernii*, and *L. wadsworthii*. Additional *Legionella* species and serogroups include those in Fields et al., *Clin. Microbiol. Rev.* 15:506-526, 2002, incorporated herein by reference. Bacterial strains may be obtained from patient or environmental samples or bacterial collections, for example, the American Type Culture Collection (Manassas, Va.).

One of ordinary skill in the art will know suitable methods for extracting nucleic acids such as RNA and/or DNA from a sample; such methods will depend upon, for example, the type of sample in which the *M. pneumoniae, C. pneumoniae*, and/or *Legionella* spp. nucleic acid is found. Nucleic acids can be extracted using standard methods. For instance, rapid nucleic acid preparation can be performed using a commercially available kit (such as kits and/or instruments from Qiagen (such as DNEasy® or RNEasy® kits), Roche Applied Science (such as MagNA Pure kits and instruments), Thermo Scientific (KingFisher mL), bioMérieux (Nuclisens® NASBA Diagnostics), or Epicentre (Masterpure™ kits)). In other examples, the nucleic acids may be extracted using guanidinium isothiocyanate, such as single-step isolation by acid guanidinium isothiocyanate-phenol-chloroform extraction (Chomczynski et al. *Anal. Biochem.* 162:156-159, 1987). The sample can be used directly or can be processed, such as by adding solvents, preservatives, buffers, or other compounds or substances.

Detecting presence of at least one of a *M. pneumoniae, C. pneumoniae*, and *Legionella* spp. nucleic acid in a sample involves contacting the sample with at least one of the probes (such as one, two, or three probes) disclosed herein that is capable of hybridizing to a *M. pneumoniae* nucleic acid (such as a *M. pneumoniae* CARDS toxin nucleic acid), a *C. pneumoniae* nucleic acid (such as a *C. pneumoniae* ArgR nucleic acid), or a *Legionella* spp. nucleic acid (such as a *Legionella* spp. SsrA nucleic acid), under conditions of very high stringency. In particular examples, the probes are detectably labeled (for example, as described in section IV, below). In some examples, the probes are at least 10, 15, 20, 25, 30, 35, or 40 nucleotides in length. In other examples, the probes may be no more than 10, 15, 20, 25, 30, 35, or 40 nucleotides in length.

In one example, the methods include contacting the sample with a first probe comprising a nucleic acid molecule between 10 and 40 nucleotides in length, wherein the first probe is capable of hybridizing under very high stringency conditions to a *M. pneumoniae* nucleic acid sequence set forth as SEQ ID NO: 1 or to a *M. pneumoniae* nucleic acid sequence set forth as SEQ ID NO: 18; contacting the sample with a second probe comprising a nucleic acid molecule between 10 and 40 nucleotides in length, wherein the second probe is capable of hybridizing under very high stringency conditions to a *C. pneumoniae* nucleic acid sequence set forth as SEQ ID NO: 2; contacting the sample with a third probe comprising a nucleic acid molecule between 10 and 40 nucleotides in length, wherein the third probe is capable of hybridizing under very high stringency conditions to a *Legionella* spp. nucleic acid sequence set forth as SEQ ID NO: 3, wherein each of the first, second, and third probes are detectably labeled; and the method further includes detecting hybridization between one or more probe and nucleic acid, wherein detection of hybridization between the first probe and a nucleic acid (such as SEQ ID NO: 1 or a portion thereof) indicates the presence of *M. pneumoniae* nucleic acid in the sample, detection of hybridization between the second probe and a nucleic acid (such as SEQ ID NO: 2 or a portion thereof) indicates the presence of *C. pneumoniae* nucleic acid in the sample, and detection of hybridization between the third probe and a nucleic acid (such as SEQ ID NO: 3 or a portion thereof) indicates the presence of *Legionella* spp. nucleic acid in the sample.

For example, the disclosed methods include contacting a sample with at least one of the probes (such as one, two, or three probes) disclosed herein (such as a nucleic acid probe capable of hybridizing under very high stringency conditions to a *M. pneumoniae* nucleic acid sequence set forth as SEQ ID NO: 1 or SEQ ID NO: 18, a *C. pneumoniae* nucleic acid sequence set forth as SEQ ID NO: 2, or a *Legionella* nucleic acid sequence set forth as SEQ ID NO: 3, for example a nucleic acid sequence at least 90% identical to the nucleotide sequence set forth as one of SEQ ID NO: 7, SEQ ID NO: 10, SEQ ID NO: 13, SEQ ID NO: 17, or SEQ ID NO: 21, such as a nucleic acid sequence consisting essentially of the nucleic acid sequence set forth as one of SEQ ID NO: 7, SEQ ID NO: 10, SEQ ID NO: 13, SEQ ID NO: 17, or SEQ ID NO: 21), and detecting hybridization between *M. pneumoniae* nucleic acid, *C. pneumoniae* nucleic acid, and/or *Legionella* spp. nucleic acid and the respective probe. In particular examples, the probes are detectably labeled (for example, as described in section IV, below). Detection of hybridization between the *M. pneumoniae* probe (for example SEQ ID NO: 7 or SEQ ID NO: 21) and *M. pneumoniae* nucleic acid indicates the presence of the *M. pneumoniae* nucleic acid in the sample, detection of hybridization between the *C. pneumoniae* probe (for example, SEQ ID NO: 10) and *C. pneumoniae* nucleic acid indicates the presence of the *C. pneumoniae* nucleic acid in the sample, and detection of hybridization between the *Legionella* probe (for example SEQ ID NO: 13 or SEQ ID NO: 17) and *Legionella* spp. nucleic acid indicates the presence of the *Legionella* spp. nucleic acid in the sample.

In some embodiments, the methods disclosed herein further include detecting the presence of a human nucleic acid, such as a human RNase P nucleic acid, for example, as an internal control for sample nucleic acid extraction, amplification, and/or detection. In particular examples, the method includes contacting the sample with a fourth probe comprising a nucleic acid molecule between 10 and 40 nucleotides in length, wherein the fourth probe is capable of hybridizing under very high stringency conditions to a human nucleic acid sequence set forth as SEQ ID NO: 4 and wherein the fourth probe is detectably labeled; and detecting hybridization between the fourth probe and a nucleic acid, wherein hybridization between the fourth probe and a nucleic acid (such as SEQ ID NO: 4 or a portion thereof) indicates the presence of human nucleic acid in the sample.

For example, detecting the presence of a human nucleic acid in a sample involves contacting the sample with a human-specific nucleic acid probe (such as the probes disclosed herein) that is capable of hybridizing to a human nucleic acid, such as a human RNase P nucleic acid under conditions of very high stringency (such as a nucleic acid probe capable of hybridizing under very high stringency conditions to a human nucleic acid sequence set forth as SEQ ID NO: 4, for example, a nucleic acid sequence set forth as SEQ ID NO: 16, such as a nucleic acid sequence consisting essentially of the nucleic acid sequence set forth as SEQ ID NO: 16), and detecting hybridization between the human nucleic acid and the probe. Detection of hybridization between the probe and the human nucleic acid indicates presence of the human nucleic acid in the sample. In some examples, detection of human nucleic acid in the sample confirms successful extraction of nucleic acids from the sample or successful amplification and detection of nucleic acids in the sample.

In some embodiments, nucleic acids present in a sample (for example, *M. pneumoniae*, *C. pneumoniae*, *Legionella* spp., and/or human nucleic acids in a sample) are amplified prior to using a hybridization probe for detection. For instance, it can be advantageous to amplify a portion of one of more of the disclosed nucleic acids, and then detect the presence of the amplified nucleic acid, for example, to increase the number of nucleic acids that can be detected, thereby increasing the signal obtained. Specific nucleic acid primers can be used to amplify a region that is at least about 50, at least about 60, at least about 70, at least about 80 at least about 90, at least about 100, at least about 200, at least about 230, at least about 300, at least about 400, at least about 500, at least about 1000, at least about 2000, or more base pairs in length to produce amplified nucleic acids (such as amplified *M. pneumoniae*-specific, *C. pneumoniae*-specific, *Legionella*-specific, or human-specific nucleic acids). In other examples, specific nucleic acid primers can be used to amplify a region that is about 50-3000 base pairs in length (for example, about 70-2000 base pairs, about 100-1000 base pairs, about 50-250 base pairs, about 300-500 base pairs, or about 1000-3000 base pairs in length).

Detecting the amplified product typically includes the use of labeled probes that are sufficiently complementary to and hybridize to the amplified nucleic acid sequence. Thus, the presence, amount, and/or identity of the amplified product can be detected by hybridizing a labeled probe, such as a fluorescently labeled probe, complementary to the amplified product. In one embodiment, the detection of a target nucleic acid sequence of interest, such as a *M. pneumoniae* CARDS toxin nucleic acid, a *C. pneumoniae* ArgR nucleic acid, or a *Legionella* spp. SsrA nucleic acid, includes the combined use of PCR amplification and a labeled probe such that the product is measured using real-time PCR (such as TaqMan® real-time PCR). In another embodiment, the detection of an amplified target nucleic acid sequence of interest includes the transfer of the amplified target nucleic acid to a solid support, such as a blot, for example a Northern blot, and probing the blot with a probe, for example a labeled probe, that is complementary to the amplified target nucleic acid sequence. In still further embodiments, the detection of amplified target nucleic acid sequence of interest includes the hybridization of a labeled amplified target nucleic acid to probes disclosed herein that are arrayed in a predetermined array with an addressable location and that are complementary to the amplified target nucleic acid.

Any nucleic acid amplification method can be used to detect the presence of one or more of *M. pneumoniae*, *C. pneumoniae*, *Legionella* spp., and/or human nucleic acids in a sample. In one specific, non-limiting example, polymerase chain reaction (PCR) is used to amplify the pathogen-specific nucleic acid sequences. In other specific, non-limiting examples, real-time PCR, reverse transcriptase-polymerase chain reaction (RT-PCR), real-time reverse transcriptase-polymerase chain reaction (rt RT-PCR), ligase chain reaction, or transcription-mediated amplification (TMA) is used to amplify the nucleic acids. In a specific example, one or more (such as 1, 2, 3, or 4) of *M. pneumoniae* CARDS toxin nucleic acid or *M. pneumoniae* orf521 nucleic acid, *C. pneumoniae* ArgR nucleic acid, *Legionella* spp. SsrA nucleic acid, and human RNase P nucleic is amplified by real-time PCR (for example, multiplex real-time PCR), for example real-time TaqMan® PCR. Techniques for nucleic acid amplification are well-known to those of skill in the art.

Typically, at least two primers are utilized in the amplification reaction. In some examples, amplification of the *M. pneumoniae* nucleic acid involves contacting the *M. pneumoniae* nucleic acid with one or more primers (such as two or more primers) that are capable of hybridizing to and directing the amplification of a *M. pneumoniae* nucleic acid, such as a primer capable of hybridizing under very high stringency conditions to a *M. pneumoniae* nucleic acid sequence set forth as SEQ NO: 1, for example a primer that is least 90% identical (such as 91%, 92%, 93%, 94%, 95%, 96%, 97%, 98%, 99%, or 100% identical) to the nucleotide sequence set forth as one of SEQ ID NO: 5 or SEQ ID NO: 6. In one example, a *M. pneumoniae* CARDS toxin nucleic acid is amplified utilizing a pair of primers, such as a forward primer at least 90% identical to SEQ ID NO: 5 and a reverse primer at least 90% identical to SEQ ID NO: 6, such as a forward primer consisting essentially of SEQ ID NO: 5 and a reverse primer consisting essentially of SEQ ID NO: 6. In other examples, amplification of the *M. pneumoniae* nucleic acid involves contacting the *M. pneumoniae* nucleic acid with one or more primers (such as two or more primers) that are capable of hybridizing to and directing the amplification of a *M. pneumoniae* nucleic acid, such as a primer capable of hybridizing under very high stringency conditions to a *M. pneumoniae* nucleic acid sequence set forth as SEQ NO: 18, for example a primer that is least 90% identical (such as 91%, 92%, 93%, 94%, 95%, 96%, 97%, 19 or SEQ ID NO: 20. In one example, a *M. pneumoniae* orf521 nucleic acid is amplified utilizing a pair of primers, such as a forward primer at least 90% identical to SEQ ID NO: 19 and a reverse primer at least 90% identical to SEQ ID NO: 20, such as a forward primer consisting essentially of SEQ ID NO: 19 and a reverse primer consisting essentially of SEQ ID NO: 20. Amplification of the *C. pneumoniae* nucleic acid involves contacting the *C. pneumoniae* nucleic acid with one or more primers (such as two or more primers) that are capable of hybridizing to and directing the amplification of a *C. pneumoniae* nucleic acid, such as a primer capable of hybridizing under very high stringency conditions to a *C. pneumoniae* nucleic acid sequence set forth as SEQ NO: 2, for example a primer that is least 90% identical (such as 91%, 92%, 93%, 94%, 95%, 96%, 97%, 98%, 99%, or 100% identical) to the nucleotide sequence set forth as one of SEQ ID NO: 8 or SEQ ID NO: 9. In one example, a *C. pneumoniae* ArgR nucleic acid is amplified utilizing a pair of primers, such as a forward primer at least 90% identical to SEQ ID NO: 8 and a reverse primer at least 90% identical to SEQ ID NO: 9, such as a forward primer consisting essentially of SEQ ID NO: 8 and a reverse primer consisting essentially of SEQ ID NO: 9. Amplification of the *Legionella* spp. nucleic acid involves contacting the *Legionella* spp. nucleic acid with one or more primers (such as two or more primers) that are capable of hybridizing to and directing the amplification of a *Legionella* spp. nucleic acid, such as a primer capable of hybridizing under very high stringency conditions to a *Legionella* spp. nucleic acid sequence set forth as SEQ NO: 3, for example a primer that is least 90% identical (such as 91%, 92%, 93%, 94%, 95%, 96%, 97%, 98%, 99%, or 100% identical) to the nucleotide sequence set forth as one of SEQ ID NO: 11 or SEQ ID NO: 12. In one example, a *Legionella* SsrA nucleic acid is amplified utilizing a pair of primers, such as a forward primer at least 90% identical to SEQ ID NO: 11 and a reverse primer at least 90% identical to SEQ ID NO: 12, such as a forward primer consisting essentially of SEQ ID NO: 11 and a reverse primer consisting essentially of SEQ ID NO: 12. Amplification of the human nucleic acid involves contacting the human nucleic acid with one or more primers (such as two or more primers) that are capable of hybridizing to and directing the amplification of a human nucleic acid, such as a primer capable of hybridizing under very high stringency conditions to a human nucleic acid sequence set forth as SEQ NO: 4, for example a primer that is least 90% identical (such as 91%, 92%, 93%, 94%, 95%, 96%, 97%, 98%, 99%, or 100% identical) to the nucleotide sequence set forth as one of SEQ ID NO: 14 or SEQ ID NO: 15. In one example, a human RNaseP nucleic acid is amplified utilizing a pair of primers, such as a forward primer at least 90% identical to SEQ ID NO: 14 and a reverse primer at least 90% identical to SEQ ID NO: 15, such as a forward primer consisting essentially of SEQ ID NO: 14 and a reverse primer consisting essentially of SEQ ID NO: 15.

The amplified *M. pneumoniae*, *C. pneumoniae*, *Legionella* spp., and/or human nucleic acid can be detected in real-time, for example by real-time PCR, in order to determine the presence, and/or the amount of *M. pneumoniae*, *C. pneumoniae*, *Legionella* spp., and/or human specific nucleic acid in a sample, such as *M. pneumoniae* CARDS toxin nucleic acid, *M. pneumoniae* orf521 nucleic acid, *C. pneumoniae* ArgR nucleic acid, *Legionella* spp. SsrA nucleic acid, or human RNase P nucleic acid. In this manner, an amplified nucleic acid sequence can be detected using a probe specific for the product amplified from the target sequence of interest, such as an amplified *M. pneumoniae* CARDS toxin nucleic acid sequence, *M. pneumoniae* orf521 nucleic acid sequence, *C. pneumoniae* ArgR nucleic acid sequence, *Legionella* spp. SsrA nucleic acid sequence, or human RNase P nucleic acid sequence. Suitable probes for real-time PCR include those described herein, such as a probe having a nucleic acid sequence at least 90% identical to SEQ ID NO: 7, 10, 13, 16, 17, or 21. In particular examples of the disclosed methods, multiplex real-time PCR is utilized to detect *M. pneumoniae*, *C. pneumoniae*, *Legionella* spp., and/or human nucleic acid present in the sample.

Real-time PCR monitors the fluorescence emitted during the reaction as an indicator of amplicon production during each PCR cycle, as opposed to endpoint detection. The real-time progress of the reaction can be viewed in some systems. Typically, real-time PCR uses the detection of a fluorescent reporter. Typically, the fluorescent reporter's signal increases in direct proportion to the amount of PCR product in a reaction. By recording the amount of fluorescence emission at each cycle, it is possible to monitor the PCR reaction during exponential phase where the first significant increase in the amount of PCR product correlates to the initial amount of target template. The higher the starting copy number of the nucleic acid target, the sooner a significant increase in fluorescence is observed.

In one embodiment, the fluorescently-labeled probes (such as probes disclosed herein) rely upon fluorescence resonance energy transfer (FRET), or in a change in the fluorescence emission wavelength of a sample, as a method to detect hybridization of a DNA probe to the amplified target nucleic acid in real-time. For example, FRET that occurs between fluorogenic labels on different probes (for example, using HybProbes) or between a donor fluorophore and an acceptor or quencher fluorophore on the same probe (for example, using a molecular beacon or a TaqMan® probe) can identify a probe that specifically hybridizes to the DNA sequence of interest and in this way, using a *M. pneumoniae* CARDS toxin probe, a *C. pneumoniae* ArgR probe, and/or a *Legionella* spp. SsrA probe, can detect the presence, and/or amount of the respective bacteria in a sample.

In some embodiments, the fluorescently-labeled DNA probes used to identify amplification products have spectrally distinct emission wavelengths, thus allowing them to be distinguished within the same reaction tube, for example in multiplex PCR, such as a multiplex real-time PCR. In some embodiments, the probes and primers disclosed herein are used in multiplex real-time PCR. For example, multiplex PCR permits the simultaneous detection of the amplification products of a *M. pneumoniae* CARDS toxin or a *M. pneumoniae* orf521, a *C. pneumoniae* ArgR, and/or a *Legionella* spp. SsrA nucleic acid using the disclosed probes or even another nucleic acid, such as a control nucleic acid, for example a human RNase P nucleic acid. Using the disclosed primers and probes, any combination of *M. pneumoniae, C. pneumoniae, Legionella* spp., and human nucleic acids can be detected.

In other examples, the probes and primers disclosed herein are used in a bead-based multiplex assay (see, e.g., U.S. Pat. No. 6,939,720). For example, probes specific for each pathogen (such as the probes disclosed herein), which are attached to different fluorescently labeled beads, are hybridized to amplified DNA from the sample. The probes will only significantly hybridize if the particular pathogen is present in the sample. The hybridized beads are then captured, for example with a biotinylated detector molecule, and the relative fluorescence of the beads for each label is measured.

In another embodiment, a melting curve analysis of the amplified target nucleic acid can be performed subsequent to the amplification process. The $T_m$ of a nucleic acid sequence depends on the length of the sequence and its G/C content. Thus, the identification of the $T_m$ for a nucleic acid sequence can be used to identify the amplified nucleic acid, for example by using double-stranded DNA binding dye chemistry, which quantitates the amplicon production by the use of a non-sequence specific fluorescent intercalating agent (such as SYBR® Green or ethidium bromide). SYBR® Green is a fluorogenic minor groove binding dye that exhibits little fluorescence when in solution but emits a strong fluorescent signal upon binding to double-stranded DNA. Typically, SYBR® Green is used in singleplex reactions, however when coupled with melting point analysis, it can be used for multiplex reactions.

Any type of thermal cycler apparatus can be used for the amplification of *M. pneumoniae, C. pneumoniae, Legionella* spp., and human nucleic acids and/or the determination of hybridization. Examples of suitable apparatuses include PTC-100® Peltier Thermal Cycler (MJ Research, Inc.; San Francisco, Calif.), a RoboCycler® 40 Temperature Cycler (Agilent/Stratagene; Santa Clara, Calif.), or GeneAmp® PCR System 9700 (Applied Biosystems; Foster City, Calif.). For real-time PCR, any type of real-time thermocycler apparatus can be used. For example, iCycler iQ™ or CFX96™ real-time detection systems (Bio-Rad, Hercules, Calif.), LightCycler® systems (Roche, Mannheim, Germany), a 7700 Sequence Detector (Perkin Elmer/Applied Biosystems; Foster City, Calif.), ABI™ systems such as the 7000, 7300, 7500, 7700, or 7900 systems (Applied Biosystems; Foster City, Calif.), or an MX4000™, MX3000™ or MX3005™ qPCR system (Agilent/Stratagene; Santa Clara, Calif.), DNA Engine Opticon® Continuous Fluorescence Detection System (Bio-Rad, Hercules, Calif.), Rotor-Gene® Q real-time cycler (Qiagen, Valencia, Calif.), or SmartCycler® system (Cepheid, Sunnyvale, Calif.) can be used to amplify nucleic acid sequences in real-time. In some embodiments, real-time PCR is performed using a TaqMan® array format, for example, a microfluidic card in which each well is pre-loaded with primers and probes for a particular target. The reaction is initiated by adding a sample including nucleic acids and assay reagents (such as a PCR master mix) and running the reactions in a real-time thermocycler apparatus.

In some embodiments, the probe is detectably labeled, either with an isotopic or non-isotopic label; in alternative embodiments, the target nucleic acid is labeled. Non-isotopic labels can, for instance, comprise a fluorescent or luminescent molecule, or an enzyme, co-factor, enzyme substrate, or hapten. The probe is incubated with a single-stranded or double-stranded preparation of RNA, DNA, or a mixture of both, and hybridization is determined. In some examples, the hybridization results in a detectable change in signal such as in increase or decrease in signal, for example from the labeled probe. Thus, detecting hybridization comprises detecting a change in signal from the labeled probe during or after hybridization relative to signal from the label before hybridization.

In some examples, the disclosed methods can predict with a sensitivity of at least 90% and a specificity of at least 90% for presence of a *M. pneumoniae* nucleic acid, such as a sensitivity of at least 91%, 92%, 93%, 94%, 95%, 96%, 97%, 98%, 99%, or even 100% and a specificity of at least of at least 91%, 92%, 93%, 94%, 95%, 96%, 97%, 98%, 99%, or even 100%. In additional examples, the disclosed methods can predict with a sensitivity of at least 90% and a specificity of at least 90% for presence of a *C. pneumoniae* nucleic acid, such as a sensitivity of at least 91%, 92%, 93%, 94%, 95%, 96%, 97%, 98%, 99%, or even 100% and a specificity of at least of at least 91%, 92%, 93%, 94%, 95%, 96%, 97%, 98%, 99%, or even 100%. In still further examples, the disclosed methods can predict with a sensitivity of at least 90% and a specificity of at least 90% for presence of a *Legionella* spp. nucleic acid, such as a sensitivity of at least 91%, 92%, 93%, 94%, 95%, 96%, 97%, 98%, 99%, or even 100% and a specificity of at least of at least 91%, 92%, 93%, 94%, 95%, 96%, 97%, 98%, 99%, or even 100%.

IV. PROBES AND PRIMERS

Probes and primers suitable for use in the disclosed methods are described herein. Such probes and primers include nucleic acid molecules capable of hybridizing to the disclosed nucleic acid molecules, such as the *M. pneumoniae* CARDS toxin sequence set forth as SEQ ID NO: 1, the *M. pneumoniae* orf521 sequence set forth as SEQ ID NO: 18, the *C. pneumoniae* ArgR sequence set forth as SEQ ID NO: 2, the *Legionella* spp. SsrA sequence set forth as SEQ ID NO: 3, or the human RNase P sequence set forth as SEQ ID NO: 4.

A. Probes

Probes capable of hybridizing to and detecting the presence of *M. pneumoniae, S. pneumoniae*, or *Legionella* spp. nucleic acid molecules, such as *M. pneumoniae* CARDS toxin nucleic acid molecules or *M. pneumoniae* orf521 nucleic acid molecules, *C. pneumoniae* ArgR nucleic acid molecules, or *Legionella* spp. SsrA nucleic acid molecules are disclosed. In some embodiments, the disclosed probes are between 10 and 40 nucleotides in length, such as 10, 11, 12, 13, 14, 15, 16, 17, 18, 19, 20, 21, 22, 23, 24, 25, 26, 27, 28 29, 30, 31, 32, 32, 34, 35, 36, 37, 38, 39, or 40 nucleotides in length and are capable of hybridizing to the disclosed nucleic acid molecules, such as the *M. pneumoniae* CARDS toxin sequence set forth as SEQ ID NO: 1, the *M. pneumoniae* orf521 sequence set forth as SEQ ID NO: 18, the *C. pneumo-* niae ArgR sequence set forth as SEQ ID NO: 2, or the Legionella spp. SsrA sequence set forth as SEQ ID NO: 3. In some examples, the probes are at least 10, 15, 20, 25, 30, 35, or 40 nucleotides in length. In other examples, the probes may be no more than 10, 15, 20, 25, 30, 35, or 40 nucleotides in length.

In several embodiments, a probe is capable of hybridizing under very high stringency conditions to a M. pneumoniae nucleic acid sequence set forth as SEQ ID NO: 1. In other embodiments, a probe is capable of hybridizing under very high stringency conditions to a C. pneumoniae nucleic acid sequence set forth as SEQ ID NO: 2. In still other embodiments, a probe is capable of hybridizing under very high stringency conditions to a Legionella nucleic acid sequence set forth as SEQ ID NO: 3.

In several embodiments, a probe capable of hybridizing to a M. pneumoniae CARDS toxin nucleic molecule includes a nucleic acid sequence that is at least 90% identical, such as at least 91%, 92%, 93%, 94%, 95%, 96%, 97%, 98%, 99%, or even 100% identical, to the nucleotide sequence set forth as TGTACCAGAGCACCCCAGAAGGGCT (SEQ ID NO: 7). In several embodiments, a probe capable of hybridizing to a M. pneumoniae CARDS toxin nucleic acid molecule consists essentially of a nucleic acid sequence set forth as SEQ ID NO: 7.

In other embodiments, a probe capable of hybridizing to a M. pneumoniae orf521 nucleic molecule includes a nucleic acid sequence that is at least 90% identical, such as at least 91%, 92%, 93%, 94%, 95%, 96%, 97%, 98%, 99%, or even 100% identical, to the nucleotide sequence set forth as TGACTGGAAGGATGTTAAGCAGGACAACAAATTT (SEQ ID NO: 21). In several embodiments, a probe capable of hybridizing to a M. pneumoniae orf521 nucleic acid molecule consists essentially of a nucleic acid sequence set forth as SEQ ID NO: 21.

In several embodiments, a probe capable of hybridizing to a C. pneumoniae ArgR nucleic molecule contains a nucleic acid sequence that is at least 90% identical, such as at least 91%, 92%, 93%, 94%, 95%, 96%, 97%, 98%, 99% or even 100% identical, to the nucleotide sequence set forth as CTTCAACAGAGAAGACCACGACCCGTCA (SEQ ID NO: 10). In several embodiments, a probe capable of hybridizing to a C. pneumoniae ArgR nucleic acid molecule consists essentially of a nucleic acid sequence set forth as SEQ ID NO: 10.

In several embodiments, a probe capable of hybridizing to a Legionella spp. SsrA nucleic molecule contains a nucleic acid sequence that is at least 90% identical, such as at least 91%, 92%, 93%, 94%, 95%, 96%, 97%, 98%, 99% or even 100% identical, to the nucleotide sequence set forth as ACGTGGGTTGC (SEQ ID NO: 13) or the nucleotide sequence as set forth as ACGATGAAAACTTTGCTGGTG (SEQ ID NO: 17). In several embodiments, a probe capable of hybridizing to a Legionella spp. SsrA nucleic acid molecule consists essentially of a nucleic acid sequence set forth as SEQ ID NO: 13 or SEQ ID NO: 17. In particular embodiments, the probe capable of hybridizing to a Legionella spp. SsrA nucleic acid molecule is capable of hybridizing to an SsrA nucleic acid molecule from any Legionella species or serogroup (for example, L. pneumophila (such as L. pneumophila serogroups Sg1, Sg2, Sg4, and Sg6), L. bozemanii, L. longbeachae, L. micdadei, L. binninghamensis, L. dumoffi, L. hackliae, L. maceachernii, L. wadsworthii, L. jordanis, L. feelii, L. cincinnatiensis, L. gonnanii, L. sainthelensi, L. tucsonensis, L. anisa, L. lansingensis, L. erythra, L. parisiensis, L. oakridgensis, L. spiritensis, L. jamestowniensis, L. santicrucis, L. cherrii, L. steigerwaltii, L. rubrilucens, L. israelensis, L. quinlivanii, L. brunensis, L. moravica, L. gratiana, L. adelaidensis, L. fairfieldensis, L. shakespearei, L. waltersii, L. genomospecies, L. quateirensis, L. worsleiensis, L. geestiana, L. natarum, L. londoniensis, L. taurinensis, L. lytica, L. drozanskii, L. rowbothamii, L. fallonii, L. gresilensis, and L beliardensis).

In several embodiments, a probe capable of hybridizing to a human RNase P nucleic molecule contains a nucleic acid sequence that is at least 90% identical, such as at least 91%, 92%, 93%, 94%, 95%, 96%, 97%, 98%, 99% or even 100% identical, to the nucleotide sequence set forth as TTCTGACCTGAAGGCTCTGCGCG (SEQ ID NO: 16). In several embodiments, a probe capable of hybridizing to a human RNase P nucleic acid molecule consists essentially of a nucleic acid sequence set forth as SEQ ID NO: 16.

In particular embodiments, the probe is detectably labeled, either with an isotopic or non-isotopic label. Non-isotopic labels can include a fluorescent or luminescent molecule, a hapten (such as biotin, dinitrophenyl, or digoxigenin), an enzyme or enzyme substrate or a chemical. Such labels are preferentially chosen such that the hybridization of the probe with a target nucleic acid (such as a M. pneumoniae nucleic acid molecule (such as CARDS toxin or orf521), a C. pneumoniae nucleic acid molecule (such as ArgR), a Legionella spp. nucleic acid molecule (such as SsrA), or a human RNase P nucleic acid molecule, or subsequence thereof) can be detected.

In some examples, the probe is labeled with one or more fluorophores. Examples of suitable fluorophore labels are provided above. In some examples, the fluorophore is a donor fluorophore. In other examples, the fluorophore is an accepter fluorophore, such as a fluorescence quencher. In some examples, the probe includes both a donor fluorophore and an accepter or quencher fluorophore, for example a donor fluorophore such as a FAM and an acceptor fluorophore such as a BLACK HOLE® quencher. Appropriate donor/acceptor fluorophore pairs can be selected using routine methods. In one example, the donor emission wavelength is one that can significantly excite the acceptor, thereby generating a detectable emission from the acceptor. In some examples, the probe is modified at the 3'-end to prevent extension of the probe by a polymerase.

In some examples, the acceptor fluorophore (such as a fluorescence quencher) is attached to the 3' end of the probe and the donor fluorophore is attached to a 5' end of the probe. In other examples, the acceptor fluorophore (such as a fluorescence quencher) is attached to the 5' end of the probe and the donor fluorophore is attached to a 3' end of the probe. In another particular example, the acceptor fluorophore (such as a fluorescence quencher) is attached to a modified nucleotide (such as a T) and the donor fluorophore is attached to a 5' end of the probe.

In particular embodiments, the probe capable of hybridizing to a M. pneumoniae CARDS toxin nucleic molecule includes a donor fluorophore attached to the 5' end and an acceptor fluorophore attached to the 3' end. In one example, the M. pneumoniae CARDS toxin probe includes the donor fluorophore HEX and the acceptor fluorophore BHQ1. In a particular example, the M. pneumoniae CARDS toxin probe consists of HEX-TGTACCAGAGCACCCCAGAAGGGCT-BHQ1 (SEQ ID NO: 7). In another embodiment, the probe capable of hybridizing to a M. pneumoniae orf521 nucleic acid includes a donor fluorophore attached to the 5' end and an acceptor fluorophore attached to the 3' end. In one example, the M. pneumoniae orf521 probe includes the donor fluorophore FAM and the acceptor fluorophore BHQ1. In a particular example, the M. pneumoniae orf521 probe consists of

FAM-TGACTGGAAGGATGTTAAGCAGGACAA-CAAATTT-BHQ1 (SEQ ID NO: 21).

In additional embodiments, the probe capable of hybridizing to a *C. pneumoniae* ArgR nucleic molecule includes a donor fluorophore attached to the 5' end and an acceptor fluorophore attached to the 3' end. In one example, the *C. pneumoniae* ArgR probe includes the donor fluorophore Quasar 670 and the acceptor fluorophore BHQ3. In a particular example, the *C. pneumoniae* ArgR probe consists of Quasar 670-CTTCAACAGAGAAGACCACGACCCGTCA-BHQ3 (SEQ ID NO: 10).

In further embodiments, the probe capable of hybridizing to a *Legionella* spp. SsrA nucleic molecule includes a donor fluorophore attached to the 5' end and an acceptor fluorophore attached to the 3' end. In one example, the *Legionella* spp. SsrA probe includes the donor fluorophore FAM and the acceptor fluorophore BHQ1. In a particular example, the *Legionella* SsrA probe consists of FAM-ACGTGGGTTGC-BHQ1 (SEQ ID NO: 13). In another example, the *Legionella* spp. SsrA probe includes the donor fluorophore FAM and a minor groove binder (MGB) acceptor fluorophore. In a particular example, the probe consists of FAM-ACGAT-GAAAACTTTGCTGGTG-MGB (SEQ ID NO: 17).

In other embodiments, the probe capable of hybridizing to a human RNase P nucleic molecule includes a donor fluorophore attached to the 5' end and an acceptor fluorophore attached to the 3' end. In one example, the human RNase P probe includes the donor fluorophore Cal Fluor Red 610 and the acceptor fluorophore BHQ2. In a particular example, the human RNase P probe consists of Cal Fluor Red 610-TTCT-GACCTGAAGGCTCTGCGCG-BHQ2 (SEQ ID NO: 16).

B. Primers

Primers capable of hybridizing to and directing the amplification of a *M. pneumoniae* nucleic acid molecule, a *C. pneumoniae* nucleic acid molecule, a *Legionella* spp. nucleic acid molecule, or a human RNase P molecule are also disclosed. The primers disclosed herein are between 10 to 40 nucleotides in length, such as 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or even 40 nucleotides in length. In some examples, the primers are at least 10, 15, 20, 25, 30, 35, or 40 nucleotides in length. In other examples, the primers may be no more than 10, 15, 20, 25, 30, 35, or 40 nucleotides in length.

In several embodiments, a primer is capable of hybridizing under very high stringency conditions to a *M. pneumoniae* CARDS toxin nucleic acid sequence, such as a *M. pneumoniae* CARDS toxin nucleic acid sequence set forth as SEQ ID NO: 1, and directing the amplification of the *M. pneumoniae* CARDS toxin nucleic acid molecule, for example amplification of SEQ ID NO: 1 or a subsequence thereof. In several embodiments, a primer is capable of hybridizing under very high stringency conditions to a *M. pneumoniae* orf521 nucleic acid sequence, such as a *M. pneumoniae* orf521 nucleic acid sequence set forth as SEQ ID NO: 18, and directing the amplification of the *M. pneumoniae* orf521 nucleic acid molecule, for example amplification of SEQ ID NO: 18 or a subsequence thereof. In several embodiments, a primer is capable of hybridizing under very high stringency conditions to a *C. pneumoniae* ArgR nucleic acid sequence, such as a *C. pneumoniae* ArgR nucleic acid sequence set forth as SEQ ID NO: 2, and directing the amplification of the *C. pneumoniae* ArgR nucleic acid molecule, for example amplification of SEQ ID NO: 2 or a subsequence thereof. In several embodiments, a primer is capable of hybridizing under very high stringency conditions to a *Legionella* spp. SsrA nucleic acid sequence, such as a *Legionella* spp. SsrA nucleic acid sequence set forth as SEQ ID NO: 3, and directing the amplification of the *Legionella* spp. SsrA nucleic acid molecule, for example amplification of SEQ ID NO: 3 or a subsequence thereof. In several embodiments, a primer is capable of hybridizing under very high stringency conditions to a human RNase P nucleic acid sequence, such as a human RNase P nucleic acid sequence set forth as SEQ ID NO: 4, and directing the amplification of the human RNase P nucleic acid molecule, for example amplification of SEQ ID NO: 4 or a subsequence thereof.

In several embodiments, a primer capable of hybridizing to and directing the amplification of a *M. pneumoniae* CARDS toxin nucleic acid molecule contains a nucleic acid sequence that is at least 90% identical, such as at least 91%, 92%, 93%, 94%, 95%, 96%, 97%, 98%, 99%, or even 100% identical, to the nucleic acid sequence set forth as TTTGGTAGCTGGT-TACGGGAAT (SEQ ID NO: 5) or GGTCGGCAC-GAATTTCATATAAG (SEQ ID NO: 6). In several embodiments, a primer capable of hybridizing to and directing the amplification of a *M. pneumoniae* CARDS toxin nucleic acid molecule consists essentially of, or consists of a nucleic acid sequence set forth as SEQ ID NO: 5 or SEQ ID NO: 6.

In several embodiments, a primer capable of hybridizing to and directing the amplification of a *M. pneumoniae* orf521 nucleic acid molecule contains a nucleic acid sequence that is at least 90% identical, such as at least 91%, 92%, 93%, 94%, 95%, 96%, 97%, 98%, 99%, or even 100% identical, to the nucleic acid sequence set forth as AAGAAGCTTATGGTA-CAGGTTGGTTAA (SEQ ID NO: 19) or TGGAGGTTGG-TAGCTAAGTAAGCA (SEQ ID NO: 20). In several embodiments, a primer capable of hybridizing to and directing the amplification of a *M. pneumoniae* orf521 nucleic acid molecule consists essentially of, or consists of a nucleic acid sequence set forth as SEQ ID NO: 19 or SEQ ID NO: 20.

In several embodiments, a primer capable of hybridizing to and directing the amplification of a *C. pneumoniae* ArgR nucleic acid molecule contains a nucleic acid sequence that is at least 90% identical, such as at least 91%, 92%, 93%, 94%, 95%, 96%, 97%, 98%, 99%, or even 100% identical, to the nucleic acid sequence set forth as CGTGGTGCTCGTTAT-TCTTTACC (SEQ ID NO: 8) or TGGCGAATAGAGAG-CACCAA (SEQ ID NO: 9). In several embodiments, a primer capable of hybridizing to and directing the amplification of a *C. pneumoniae* ArgR nucleic acid molecule consists essentially of, or consists of a nucleic acid sequence set forth as SEQ ID NO: 8 or SEQ ID NO: 9.

In several embodiments, a primer capable of hybridizing to and directing the amplification of a *Legionella* spp. SsrA nucleic acid molecule contains a nucleic acid sequence that is at least 90% identical, such as at least 91%, 92%, 93%, 94%, 95%, 96%, 97%, 98%, 99%, or even 100% identical, to the nucleic acid sequence set forth as GGCGACCTGGCTTC (SEQ ID NO: 11) or TATGACCGTTGATTCGATACC (SEQ ID NO: 12). In several embodiments, a primer capable of hybridizing to and directing the amplification of a *Legionella* spp. SsrA nucleic acid molecule consists essentially of, or consists of a nucleic acid sequence set forth as SEQ ID NO: 11 or SEQ ID NO: 12. In particular embodiments, the primer capable of hybridizing to and directing amplification of a *Legionella* spp. SsrA nucleic acid molecule (such as SEQ ID NO: 11 or SEQ ID NO: 12) is capable of hybridizing to an SsrA nucleic acid molecule from any *Legionella* species (for example, *L. pneumophila* (such as *L. pneumophila* subtypes Sg1, Sg2, Sg4, and Sg6), *L. bozemanii, L. longbeachae, L. micdadei, L. birminghamensis, L. dumoffi, L. hackliae, L. maceachernii, L. wadsworthii, L. jordanis, L. feelii, L. cincinnatiensis, L. gormanii, L. sainthelensis, L. tucsonensis, L.* anisa, *L. lansingensis, L. erythra, L. parisiensis, L. oakridgensis, L. spiritensis, L. jamestwoniensis, L. santicrucis, L. cherrii, L. steigerwaltii, L. rubrilucens, L. israelensis, L. quinlivanii, L. brunensis, L. moravica, L. gratiana, L. adelaidensis, L. fairfieldensis, L. shakespearei, L. waltersii, L. genomospecies, L. quateirensis, L. worsleiensis, L. geestiana, L. natarum, L. londoniensis, L. taurinensis, L. lytica, L. drozanskii, L. rowbothamii, L. fallonii, L. gresilensis*, and *L beliardensis*).

In several embodiments, a primer capable of hybridizing to and directing the amplification of a human RNase P nucleic acid molecule contains a nucleic acid sequence that is at least 90% identical, such as at least 91%, 92%, 93%, 94%, 95%, 96%, 97%, 98%, 99%, or even 100% identical, to the nucleic acid sequence set forth as AGATTTGGACCTGCGAGCG (SEQ ID NO: 14) or GAGCGGCTGTCTCCACAAGT (SEQ ID NO: 15). In several embodiments, a primer capable of hybridizing to and directing the amplification of a human RNase P nucleic acid molecule consists essentially of, or consists of a nucleic acid sequence set forth as SEQ ID NO: 14 or SEQ ID NO: 15.

In certain embodiments, the primers are a set of primers, such as a pair of primers, capable of hybridizing to and amplifying a *M. pneumoniae* CARDS toxin nucleic acid molecule, a *C. pneumoniae* ArgR nucleic acid molecule, a *Legionella* spp. SsrA nucleic acid molecule, or a human RNase P nucleic acid molecule. Such a set of primers includes at least one forward primer and a least one reverse primer, where the primers are specific for the amplification of a *M. pneumoniae* CARDS toxin nucleic acid molecule, a *C. pneumoniae* ArgR nucleic acid molecule, a *Legionella* spp. SsrA nucleic acid molecule, and/or a human RNase P nucleic acid molecule.

In some examples, the set of primers includes a pair of primers that is specific for the amplification of a *M. pneumoniae* nucleic acid molecule that includes a portion of the nucleic acid sequence of the *M. pneumoniae* CARDS toxin gene, such as the nucleic acid sequence set forth as SEQ ID NO: 1. In certain examples, the pair of primers includes a forward primer at least 90% identical to SEQ ID NO: 5, such as at least 91%, 92%, 93%, 94%, 95%, 96%, 97%, 98%, or 99% identical to SEQ ID NO: 5, and a reverse primer at least 90% identical to SEQ ID NO: 6, such as at least 91%, 92%, 93%, 94%, 95%, 96%, 97%, 98%, or 99% identical to SEQ ID NO: 6.

In some examples, the set of primers includes a pair of primers that is specific for the amplification of a *M. pneumoniae* nucleic acid molecule that includes a portion of the nucleic acid sequence of the *M. pneumoniae* orf521 gene, such as the nucleic acid sequence set forth as SEQ ID NO: 18. In certain examples, the pair of primers includes a forward primer at least 90% identical to SEQ ID NO: 19, such as at least 91%, 92%, 93%, 94%, 95%, 96%, 97%, 98%, or 99% identical to SEQ ID NO: 19, and a reverse primer at least 90% identical to SEQ ID NO: 20, such as at least 91%, 92%, 93%, 94%, 95%, 96%, 97%, 98%, or 99% identical to SEQ ID NO: 20.

In some examples, the set of primers includes a pair of primers that is specific for the amplification of a *C. pneumoniae* nucleic acid molecule that includes a portion of the nucleic acid sequence of the *C. pneumoniae* ArgR gene, such as the nucleic acid sequence set forth as SEQ ID NO: 2. In certain examples, the pair of primers includes a forward primer at least 90% identical to SEQ ID NO: 8, such as at least 91%, 92%, 93%, 94%, 95%, 96%, 97%, 98%, or 99% identical to SEQ ID NO: 8, and a reverse primer at least 90% identical to SEQ ID NO: 9, such as at least 91%, 92%, 93%, 94%, 95%, 96%, 97%, 98%, or 99% identical to SEQ ID NO: 9.

In some examples, the set of primers includes a pair of primers that is specific for the amplification of a *Legionella* spp. nucleic acid molecule that includes a portion of the nucleic acid sequence of the *Legionella* spp. SsrA gene, such as the nucleic acid sequence set forth as SEQ ID NO: 3. In certain examples, the pair of primers includes a forward primer at least 90% identical to SEQ ID NO: 11, such as at least 91%, 92%, 93%, 94%, 95%, 96%, 97%, 98%, or 99% identical to SEQ ID NO: 11, and a reverse primer at least 90% identical to SEQ ID NO: 12, such as at least 91%, 92%, 93%, 94%, 95%, 96%, 97%, 98%, or 99% identical to SEQ ID NO: 12.

In some examples, the set of primers includes a pair of primers that is specific for the amplification of a human nucleic acid molecule that includes a portion of the nucleic acid sequence of the human RNase P gene, such as the nucleic acid sequence set forth as SEQ ID NO: 4. In certain examples, the pair of primers includes a forward primer at least 90% identical to SEQ ID NO: 14, such as at least 91%, 92%, 93%, 94%, 95%, 96%, 97%, 98%, or 99% identical to SEQ ID NO: 14, and a reverse primer at least 90% identical to SEQ ID NO: 15, such as at least 91%, 92%, 93%, 94%, 95%, 96%, 97%, 98%, or 99% identical to SEQ ID NO: 15.

Although exemplary probe and primer sequences are provided in SEQ ID NOs: 5-17 and 19-21, the primer and/or probe sequences can be varied slightly by moving the probe or primer a few nucleotides upstream or downstream from the nucleotide positions that they hybridize to on the target nucleic molecule acid, provided that the probe and/or primer is still specific for the target nucleic acid sequence, for example specific for SEQ ID NO: 1, SEQ ID NO: 2, SEQ ID NO: 3, SEQ ID NO: 4, or SEQ ID NO: 18. For example, variations of the probes and primers disclosed as SEQ ID NOs: 5-17 and 19-21 can be made by "sliding" the probes and/or primers a few nucleotides 5' or 3' from their positions, and such variation will still be specific for the respective target nucleic acid sequence.

Also provided by the present disclosure are probes and primers that include variations to the nucleotide sequences shown in any of SEQ ID NOs: 5-17 and 19-21, as long as such variations permit detection of the target nucleic acid molecule. For example, a probe or primer can have at least 90% sequence identity such as at least 91%, 92%, 93%, 94%, 95%, 96%, 97%, 98%, or 99% identity to a nucleic acid consisting of the sequence shown in any of SEQ ID NOs: 5-17 and 19-21. In such examples, the number of nucleotides does not change, but the nucleic acid sequence shown in any of SEQ ID NOs: 5-17 and 19-21 can vary at a few nucleotides, such as changes at 1, 2, 3, or 4 nucleotides.

The present application also provides probes and primers that are slightly longer or shorter than the nucleotide sequences shown in any of SEQ ID NOs: 5-17 and 19-21, as long as such deletions or additions permit detection of the desired target nucleic acid molecule, such as a *M. pneumoniae* CARDS toxin sequence, a *M. pneumoniae* orf521 sequence, a *C. pneumoniae* ArgR sequence, a *Legionella* SsrA sequence, or a human RNase P sequence. For example, a probe or primer can include a few nucleotide deletions or additions at the 5'- or 3'-end of the probe or primers shown in any of SEQ ID NOs: 5-17 and 19-21, such as addition or deletion of 1, 2, 3, or 4 nucleotides from the 5'- or 3'-end, or combinations thereof (such as a deletion from one end and an addition to the other end). In such examples, the number of nucleotides changes.

Also provided are probes and primers that are degenerate at one or more positions (such as 1, 2, 3, 4, 5, or more positions), for example, a probe or primer that includes a mixture of nucleotides (such as 2, 3, or 4 nucleotides) at a specified position in the probe or primer. In some examples, the probes and primers disclosed herein include one or more synthetic bases or alternative bases (such as inosine). In other examples, the probes and primers disclosed herein include one or more modified nucleotides or nucleic acid analogues, such as one or more locked nucleic acids (see, e.g., U.S. Pat. No. 6,794,499) or one or more superbases (Nanogen, Inc., Bothell, Wash.). In a specific example, a probe that hybridizes to a *Legionella* SsrA nucleic acid (such as SEQ ID NO: 13) includes one or more locked nucleic acids, for example as shown in Table 1, below. In other examples, the probes and primers disclosed herein include a minor groove binder conjugated to the 5' or 3' end of the oligonucleotide (see, e.g., U.S. Pat. No. 6,486,308).

V. KITS

The nucleic acid primers and probes disclosed herein can be supplied in the form of a kit for use in the detection of one or more of *M. pneumoniae*, *C. pneumoniae*, and *Legionella* spp. in a sample. In such a kit, an appropriate amount of one or more of the nucleic acid probes and/or primers (such as *M. pneumoniae* CARDS toxin, *C. pneumoniae* ArgR, and *Legionella* spp. SsrA probes and primers as disclosed herein, for example SEQ ID NOs: 5-17) are provided in one or more containers. A nucleic acid probe and/or primer may be provided suspended in an aqueous solution or as a freeze-dried or lyophilized powder, for instance. The container(s) in which the nucleic acid(s) are supplied can be any conventional container that is capable of holding the supplied form, for instance, microfuge tubes, ampoules, or bottles. The kits can include either labeled or unlabeled nucleic acid probes for use in detection of *M. pneumoniae*, *C. pneumoniae*, and *Legionella* spp. nucleic acids. One or more control probes and/or primers for use in the PCR reactions also may be supplied in the kit (for example, for the detection of human RNase P). In some examples, the probes are detectably labeled.

In some examples, one or more sets of primers (such as the primers described above), such as pairs of primers (for example, one pair, two pairs, three pairs, or four pairs of primers), may be provided in pre-measured single use amounts in individual, typically disposable, tubes or equivalent containers. With such an arrangement, the sample to be tested for the presence of the target nucleic acids can be added to the individual tube(s) and amplification carried out directly.

The amount of nucleic acid primer supplied in the kit can be any appropriate amount, and may depend on the target market to which the product is directed. For instance, if the kit is adapted for research or clinical use, the amount of each nucleic acid primer provided would likely be an amount sufficient to prime several PCR amplification reactions. General guidelines for determining appropriate amounts may be found in Innis et al., Sambrook et al., and Ausubel et al. A kit may include more than two primers in order to facilitate the PCR amplification of a larger number of target nucleic acid molecules, such as *M. pneumoniae*, *C. pneumoniae*, *Legionella* spp., and/or human nucleic acids.

In some embodiments, kits also may include the reagents necessary to carry out PCR amplification reactions, including DNA sample preparation reagents, appropriate buffers (such as polymerase buffer), salts (for example, magnesium chloride), deoxyribonucleotides (dNTPs), and polymerases.

In particular embodiments, the kit includes prepackaged probes, such as probes suspended in suitable medium in individual containers (for example, individually sealed tubes). In some examples, the probes include those provided herein. In other particular embodiments, the kit includes equipment, reagents, and instructions for extracting and/or purifying nucleotides from a sample.

The present disclosure is illustrated by the following non-limiting Examples.

EXAMPLE 1

Primer and Probe Design and Clinical Specimens

The primers and probes for *Mycoplasma pneumoniae* CARDS toxin (MP181) and human RNase P have been previously described (Winchell et al., *J. Clin. Microbiol.* 46:3116-3118, 2008; Emery et al., Lab. Studies 10:311-316, 2004). *Legionella* spp. primers and probe (Pan-Leg) were designed manually targeting the SsrA gene (GenBank accession number U68079) and tested against all known *Legionella* species and serogroups (Fields et al., *Clin. Microbiol. Rev.* 15:506-526, 2002). Primer Express® Software Version 3.0 (Applied Biosystems, Foster City, Calif.) was used to design primer and probe sequences targeting the arginine repressor protein gene (ArgR) of *Chlamydophila pneumoniae* (GenBank accession no. NP_876472.1; CP-Arg). CP-Arg was tested against numerous strains of *C. pneumoniae* including: AR-388, BR-393, W6, IOL-207, FML-7, FML-12, FML-16, FML-19, K66, TW-183, CM1 CWL-029, TW-2043, TW-2023, CWL-011, CWL-050, and BAL-16.

Primer and probe sequences are shown in Table 1. For multiplex PCR, probes were labeled as follows: MP181-P (SEQ ID NO: 7), 5'-HEX and 3'-BHQ1; CP-Arg-P (SEQ ID NO: 10), 5'-Quasar 670 and 3'-BHQ3; Pan-Leg-P (SEQ ID NO: 13), 5'-FAM and 3'-BHQ1; and RNaseP-P (SEQ ID NO: 16), 5'-Cal Fluor Red 610 and 3'-BHQ2. Primers and probes were obtained from the Centers for Disease Control Biotechnology Core Facility, Biosearch Technologies (Novato, Calif.), or IDT (Coralville, Iowa).

TABLE 1

Real-time PCR Primers and Probes

| Primer/Probe | Target | Product (bp) | Sequence (5' to 3') | SEQ ID NO: |
|---|---|---|---|---|
| *M. pneumoniae* | CARDS toxin | 73 | | |
| MP181-F | | | TTTGGTAGCTGGTTACGGGAAT | 5 |
| MP181-R | | | GGTCGGCACGAATTTCATATAAG | 6 |
| MP181-P | | | TGTACCAGAGCACCCCAGAAGGGCT | 7 |

TABLE 1-continued

Real-time PCR Primers and Probes

| Primer/Probe | Target | Product (bp) | Sequence (5' to 3') | SEQ ID NO: |
|---|---|---|---|---|
| C. pneumoniae | ArgR | 74 | | |
| CP-Arg-F | | | CGTGGTGCTCGTTATTCTTTACC | 8 |
| CP-Arg-R | | | TGGCGAATAGAGAGCACCAA | 9 |
| CP-Arg-P | | | CTTCAACAGAGAAGACCACGACCCGTCA | 10 |
| Legionella spp.SsrA | | 230 | | |
| Pan-Leg-F | | | GGCGACCTGGCTTC | 11 |
| Pan-Leg-R | | | TATGACCGTTGATTCGATACC | 12 |
| Pan-Leg-P | | | A<u>C</u>G<u>T</u>GGG<u>T</u>TGC$^a$ | 13 |
| Human | RNaseP | 62 | | |
| RNaseP-F | | | AGATTTGGACCTGCGAGCG | 14 |
| RNaseP-R | | | GAGCGGCTGTCTCCACAAGT | 15 |
| RNaseP-P | | | TTCTGACCTGAAGGCTCTGCGCG | 16 |

$^a$Underlined bases indicate a locked nucleic acid

Respiratory clinical specimens were obtained from previous respiratory surveillance studies and outbreak investigations. Clinical sensitivity was established by testing 177 nasopharyngeal and/or oropharyngeal swabs by all four singleplex assays as well as the multiplex assay (Example 2). Twenty additional specimens were tested with the Pan-Leg singleplex assay along with the multiplex assay. These included lung tissue, bronchial lavage, sputums, a bronchial swab, an oropharyngeal swab and two samples of unknown origin. Study specimens were extracted using either the MagNA Pure™ LC 1.0 Instrument (Roche Applied Science, Indianapolis, Ind.) or the KingFisher® mL instrument (Thermo Scientific, Rochester, N.Y.). For the MagNA Pure™ LC the Total Nucleic Acid Isolation Kit was used following the manufacturer's instructions for the Total NA Serum_Plasma_Blood protocol with a 200 µl sample volume and 100 µl elution volume. For the KingFisher® mL, the InviMag® Bacteria DNA Mini kit was used (Invitek, Germany) following the manufacturer's instructions. All clinical specimens were tested in triplicate with both the multiplex assay and target-specific singleplex assays.

EXAMPLE 2

Real-Time PCR Assays

Primers and probes were initially tested for each organism in real-time singleplex PCR. For each singleplex assay, the probes were labeled with 6-carboxyfluorescein (FAM) and were examined separately under previously optimized conditions. The 25 µl reaction volume contained: 12.5 µl Platinum Quantitative PCR Supermix-UNG (Life Technologies/Invitrogen, Carlsbad, Calif.), 3 mM $MgCl_2$, 1 µl 10 mM nucleotide mix (Promega, Madison, Wis.), 1 µM of each primer, 200 nM of probe, 1.25 U Platinum Taq Polymerase (Life Technologies/Invitrogen, Carlsbad, Calif.), and 5 µl template (serial dilutions from 100 µg to 1 µg DNA). Each assay (six replicates per dilution) was performed on an ABI 7500 Real-Time PCR system using the following thermocycling conditions: 95° C. for 2 minutes, followed by 45 cycles of 95° C. for 15 seconds and 60° C. for 1 minute.

The multiplex assay used identical primer and probe sequences as used in the singleplex assays, however all oligonucleotides were pooled in a single tube reaction. A combined positive control (CPC) containing M. pneumoniae, C. pneumoniae, L. pneumophila Sg 1, and human nucleic acid was used to determine which fluorophores were optimal for each assay. Probes were labeled as described in Example 1. Final concentrations of each primer and probe set were 250 nM each for MP181-F, MP181-R, CP-Arg-F, CP-Arg-R, RNaseP-F, and RNaseP-R; 125 nM each for Pan-Leg-F and Pan-Leg-R; 100 nM for MP-181-P; 50 nM each for CP-Arg-P and RNaseP-P; and 25 nM for Pan-Leg-P. The multiplex reaction contained 12.5 µl PerfeCTa™ Multiplex qPCR SuperMix (Quanta Biosciences, Gaithersburg, Md.), the appropriate volume of each primer and probe, and 5 µl template, to a final volume of 25 µl. The assay was performed on the ABI™ 7500 Real-Time PCR system using the thermocycling conditions described above, except the initial activation step was extended to 5 minutes, as recommended by the manufacturer.

Analytical sensitivity was established by testing a dilution series of nucleic acids for each assay. M. pneumoniae M129, C. pneumoniae TW-183, and L. pneumophila Sg1 were grown on appropriate media or in cells. Nucleic acid extractions were performed using the QIAamp® DNA Blood Mini Kit (Qiagen, Valencia, Calif.) following manufacturer's instructions. Nucleic acid concentrations for each extraction were determined using the NanoDrop® ND-1000 V3.5.2 Spectrophotometer (NanoDrop products, Wilmington, Del.). All nucleic acid extracts and human DNA (Promega, Madison, Wis.) were initially diluted to 1 ng/µl in Tris-EDTA, pH 7.0 followed by ten-fold dilutions down to 1 fg/µl. Each dilution series was tested in triplicate with the appropriate singleplex assay as well as the multiplex assay as described. Limits of Detection (LODs) were established for each assay and defined as the lowest dilution in which all three replicates had a positive crossing threshold cycle ($C_g$).

Analytical specificity for each assay was verified using a comprehensive panel of related respiratory organisms, each at a concentration of 3 ng/µl. The panel included: Mycoplasma faecium, M. lipophilum, M. salivarium, M. pirum, M. orale, M. penetrans, M. genitalium, M. hominis, M. fermentans, M. buccale, M. arginini, M. hyorhinis, M. amphoriforme, Lactobacillus planitarium, Staphylococcus epidermidis, Coxiella burnetii, Streptococcus salivarius, Bordetella pertussis, Legionella pneumophila, L. bozemanii, L. longbeachae, L. micdadei, L. binninghamensis, L. dumoffi, L. hackliae, L. maceachemii, L. wadsworthii, L. jordanis, L. feelii, L. cincinnatiensis, L. gormanii, L. sainthelensi, L. tucsonensis, L. anisa, L. lansingensis, L. erythra, L. parisiensis, L. oakridgensis, L. spiritensis, L. jamestwoniensis, L. santicrucis, L. cherrii, L. steigerwaltii, L. rubrilucens, L. israelensis, L. quinlivanii, L. brunensis, L. moravica, L. gratiana, L. adelaidensis, L. fairfieldensis, L. shakespearei, L. waltersii, L. genomospecies, L. quateirensis, L. worsleiensis, L. geestiana, L. natarum, L. londoniensis, L. taurinensis, L. lytica, L. drozanskii, L. rowbothamii, L. fallonii, L. gresilensis, L. beliardensis, Streptococcus pneumoniae, Ureaplasma urealyticum, Neisseria meningitidis, Chlamydia trachomatis, Chlamydophila psittaci, Chlamydophila pneumoniae, Streptococcus pyogenes, Haemophilus influenzae, Neisseria elongata, Pseudomonas aeruginosa, Moraxella catarrhalis, Mycobacterium tuberculosis, Candida albicans, Escherichia coli, Staphylococcus aureus, Ureaplasma parvum, human DNA, human coronavirus, human rhinovirus, human parainfluenza virus 2, human parainfluenza virus 3, human adenovirus, influenza virus A, influenza virus B, respiratory syncytial virus A, and respiratory syncytial virus B. No cross-reactivity or non-specific amplification was observed for any of the assays tested with these organisms.

Figure 3:
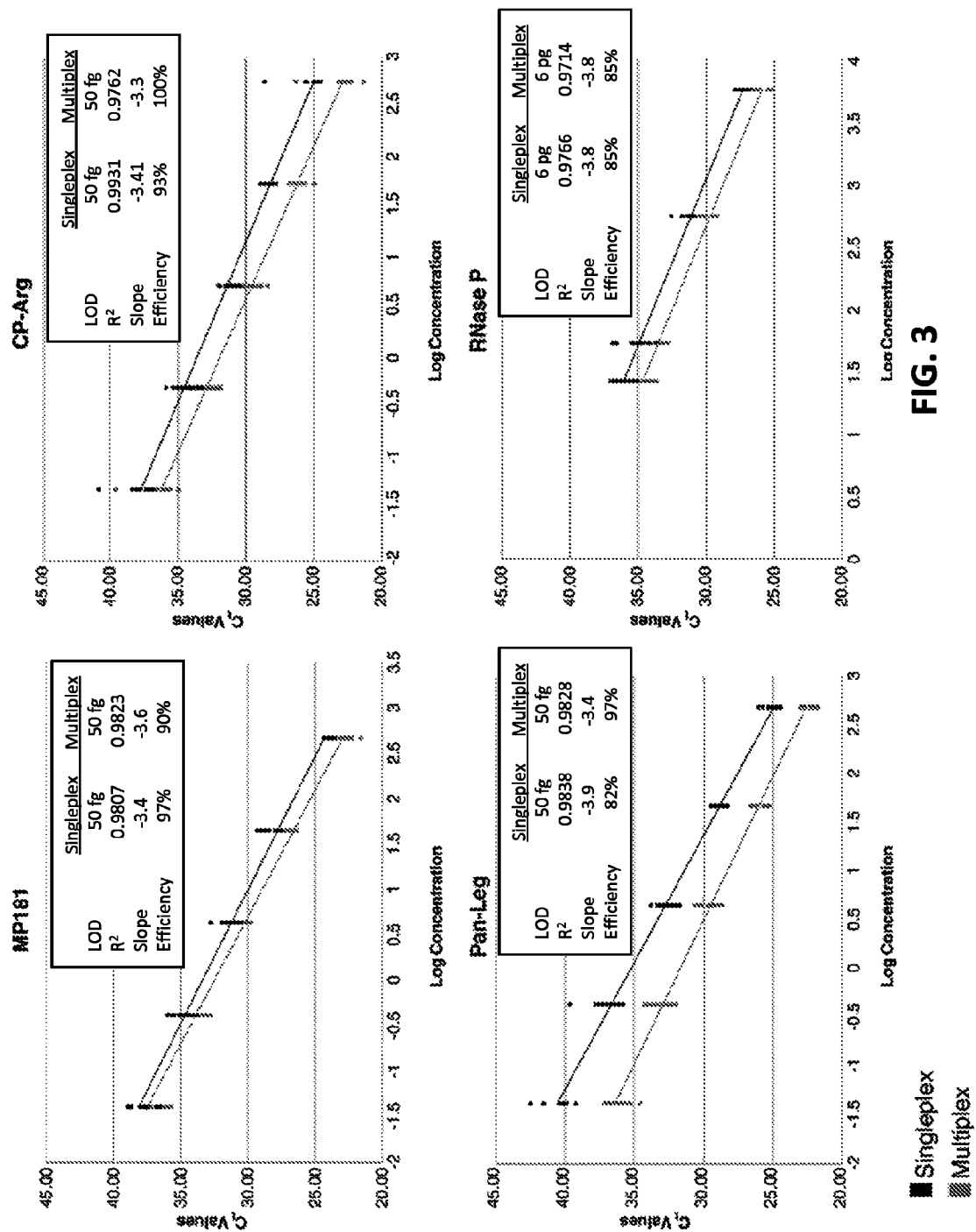
FIG. 3 is a series of graphs showing a comparison of multiplex versus singleplex assay performance for each of MP181, CP-Arg, Pan-Leg, and RNase P assays.

A comparison of the multiplex versus singleplex assays for all four markers including analytical sensitivity, correlation values, and assay efficiencies is shown in FIG. 3. The limits of detection were equivalent for the singleplex and multiplex pathogen-specific assays (50 fg) as well as for the RNase P assay (6 pg). Efficiencies ranges from 82% to 100% depending on the target. The efficiencies for both CP-Arg and Pan-Leg were higher with the multiplex assay versus singleplex at 100% versus 93% and 97% versus 82%, respectively. RNase P efficiencies were identical with each assay (85%), while the MP181 singleplex assay efficiency was higher at 97% versus the multiplex.

Table 2 shows the average $C_t$ values with standard deviations (SD) for all positive clinical specimens using the multiplex and singleplex assays for all bacterial targets. A total of 197 respiratory specimens were tested using both assays. Of these, 36 specimens tested positive for C. pneumoniae, 23 were positive for M. pneumoniae and 17 were positive for Legionella spp. The remaining specimens were negative in all three replicates for these agents when tested in both assays. All specimens gave amplification curves with the RNase P marker for both the multiplex and singleplex assays with a Ct range of 22.20-31.99 and 23.64-33.03 respectively.

Statistical analysis was performed to determine if the multiplex assay provided a significant improvement in performance upon testing clinical specimens. The CP-Arg, Pan-Leg, and RNase P assays all showed significant differences using the student's t-test with $p<0.0002$. The CP-Arg multiplex assay consistently displayed lower Ct values (22.37-38.06) vs. the singleplex assay (23.43-39.13). Similarly, the Pan-Leg multiplex assay exhibited lower Ct values, with a range of 20.53-36.67 vs. 22.52-40.32 for the singleplex assay. The student's t test for the MP181 marker showed no statistical difference with a $p=0.030$. Statistical analysis was not performed on specimens that failed to provide positive growth curves in all three replicates with either the singleplex or multiplex assay. Eight specimens tested with the CP-Arg singleplex assay failed to have growth curves in all three replicates, however the multiplex assay was able to detect four of these in all three replicates. Furthermore, the multiplex assay was able to detect an additional C. pneumoniae positive specimen (in 1 of 3 replicates) that was missed by the singleplex reaction. The M. pneumoniae specific assay (MP181) showed equivalent sensitivity with both assays detecting less than 3 replicates in the same 4 specimens. Lastly, one of twenty Pan-Leg positive specimens showed less than three replicates positive with both assays, although the Ct value for the multiplex assay (38.08) was significantly earlier than that of the singleplex assay (43.47).

TABLE 2

Real-Time PCR Results for Clinical Specimens

| | C. pneumoniae (CP-Arg) | | M. pneumoniae (MP181) | | Legionella (Pan-Leg) | |
| --- | --- | --- | --- | --- | --- | --- |
| Specimen | Singleplex | Multiplex | Singleplex | Multiplex | Singleplex | Multiplex |
| 1 | 37.04 ± 0.97 | 35.04 ± 0.35 | | | | |
| 2 | 28.20 ± 0.09 | 26.38 ± 0.07 | | | | |
| 3 | 32.33 ± 0.05 | 30.18 ± 0.16 | | | | |
| 4 | 38.03 ± 0.78 | 35.90 ± 0.51 | | | | |
| 5 | 35.11 ± 0.24 | 32.79 ± 0.27 | | | | |
| 6 | 33.37 ± 0.30 | 31.19 ± 0.51 | | | | |
| 7 | 35.68 ± 0.43 | 33.12 ± 0.36 | | | | |
| 8 | 35.19 ± 0.07 | 33.03 ± 0.26 | | | | |
| 9 | 34.97 ± 0.18 | 33.10 ± 0.45 | | | | |
| 10 | 35.90 ± 0.44 | 35.36 ± 0.27 | | | | |
| 11 | 25.19 ± 0.10 | 23.76 ± 0.17 | | | | |
| 12 | 33.39 ± 0.20 | 31.42 ± 0.09 | | | | |
| 13 | 37.50 ± 0.36 | 35.49 ± 0.10 | | | | |
| 14 | 30.42 ± 0.17 | 28.16 ± 0.25 | | | | |
| 15 | 31.47 ± 0.38 | 29.41 ± 0.05 | | | | |
| 16 | 24.49 ± 0.08 | 23.32 ± 0.11 | | | | |
| 17 | 32.73 ± 0.13 | 31.71 ± 0.17 | | | | |
| 18 | 36.35 ± 0.86 | 35.31 ± 0.24 | | | | |
| 19 | 39.03 ± 0.26 | 35.21 ± 0.71 | | | | |
| 20 | 26.29 ± 0.14 | 24.69 ± 0.16 | | | | |
| 21 | 30.42 ± 0.17 | 28.89 ± 0.15 | | | | |
| 22 | 23.43 ± 0.11 | 22.37 ± 0.20 | | | | |
| 23 | 39.06 ± 0.87 | 36.02 ± 0.51 | | | | |
| 24 | 33.60 ± 0.21 | 31.33 ± 0.16 | | | | |
| 25 | 37.93 ± 0.88 | 38.06 ± 0.01 | | | | |
| 26 | 37.15 ± 0.79 | 34.93 ± 0.73 | | | | |
| 27 | 36.91 ± 0.90 | 35.83 ± 0.73 | | | | |

TABLE 2-continued

Real-Time PCR Results for Clinical Specimens

| | C. pneumoniae (CP-Arg) | | M. pneumoniae (MP181) | | Legionella (Pan-Leg) | |
|---|---|---|---|---|---|---|
| Specimen | Singleplex | Multiplex | Singleplex | Multiplex | Singleplex | Multiplex |
| 28 | 44.10 ± 1.09* | 40.40 ± 3.18 | | | | |
| 29 | 39.56 ± 1.41* | 43.70 ± 1.11 | | | | |
| 30 | 38.20 ± 1.01* | 35.59 ± 0.16 | | | | |
| 31 | 38.92 ± 0.28* | 35.97 ± 0.54 | | | | |
| 32 | 38.76** | 35.89 ± 0.59* | | | | |
| 33 | 38.23** | 36.65 ± 2.33* | | | | |
| 34 | 38.97** | 36.66 ± 0.77* | | | | |
| 35 | 39.44 ± 0.07* | 37.99 ± 0.96* | | | | |
| 36 | | 37.48** | | | | |
| 37 | | | 33.69 ± 0.09 | 34.62 ± 0.67 | | |
| 38 | | | 29.59 ± 0.06 | 29.72 ± 0.15 | | |
| 39 | | | 29.16 ± 0.04 | 29.02 ± 0.12 | | |
| 40 | | | 31.93 ± 0.11 | 31.65 ± 0.30 | | |
| 41 | | | 29.83 ± 0.23 | 29.91 ± 0.06 | | |
| 42 | | | 31.12 ± 0.12 | 36.40 ± 0.05 | | |
| 43 | | | 34.58 ± 0.41 | 34.37 ± 0.16 | | |
| 44 | | | 35.79 ± 0.64 | 36.14 ± 0.92 | | |
| 45 | | | 36.91 ± 0.94 | 36.10 ± 1.24 | | |
| 46 | | | 33.49 ± 0.22 | 33.21 ± 0.11 | | |
| 47 | | | 30.88 ± 0.21 | 31.54 ± 0.16 | | |
| 48 | | | 37.65 ± 0.60 | 38.17 ± 0.46 | | |
| 49 | | | 30.03 ± 0.19 | 28.27 ± 0.21 | | |
| 50 | | | 36.78 ± 0.29 | 36.60 ± 0.99 | | |
| 51 | | | 23.03 ± 0.14 | 22.59 ± 0.09 | | |
| 52 | | | 34.71 ± 1.15 | 35.04 ± 0.98 | | |
| 53 | | | 32.11 ± 0.06 | 32.46 ± 0.30 | | |
| 54 | | | 35.94 ± 0.47 | 35.60 ± 0.70 | | |
| 55 | | | 38.27 ± 0.54* | 40.76 ± 1.19 | | |
| 56 | | | 38.04 ± 0.12* | 40.32** | | |
| 57 | | | 37.85 ± 0.09* | 39.53** | | |
| 58 | | | 37.98 ± 1.14 | 38.82 ± 1.85* | | |
| 59 | | | 37.92 ± 0.44 | 37.63 ± 0.98* | | |
| 60 | | | | | 31.67 ± 0.07 | 28.56 ± 0.24 |
| 61 | | | | | 35.61 ± 0.19 | 32.08 ± 0.45 |
| 62 | | | | | 38.36 ± 0.13 | 35.61 ± 1.66 |
| 63 | | | | | 38.20 ± 0.20 | 35.31 ± 0.19 |
| 64 | | | | | 29.88 ± 0.14 | 27.38 ± 0.38 |
| 65 | | | | | 38.39 ± 0.55 | 35.37 ± 0.46 |
| 66 | | | | | 31.43 ± 0.43 | 27.82 ± 0.30 |
| 67 | | | | | 30.47 ± 0.05 | 27.62 ± 0.29 |
| 68 | | | | | 32.47 ± 0.23 | 28.55 ± 0.39 |
| 69 | | | | | 29.99 ± 0.12 | 26.88 ± 0.09 |
| 70 | | | | | 27.58 ± 0.16 | 24.75 ± 0.36 |
| 71 | | | | | 40.32 ± 0.21 | 36.67 ± 0.30 |
| 72 | | | | | 22.51 ± 0.26 | 20.53 ± 0.23 |
| 73 | | | | | 34.92 ± 0.61 | 33.60 ± 0.98 |
| 74 | | | | | 37.34 ± 0.31 | 34.54 ± 0.83 |
| 75 | | | | | 36.36 ± 0.94 | 33.76 ± 0.16 |
| 76 | | | | | 43.47** | 38.08** |

Figure 1B:
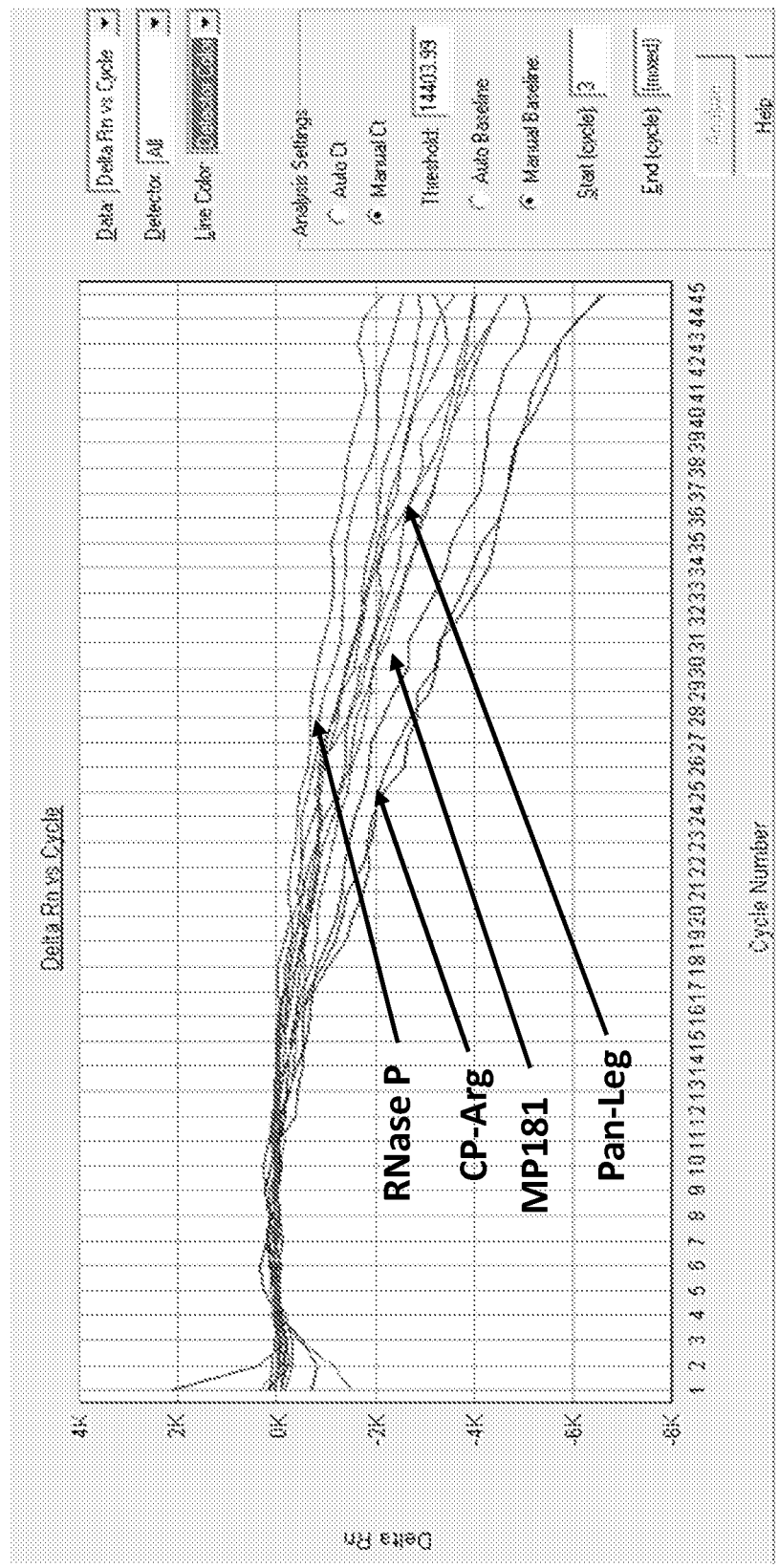
Figure 2A:
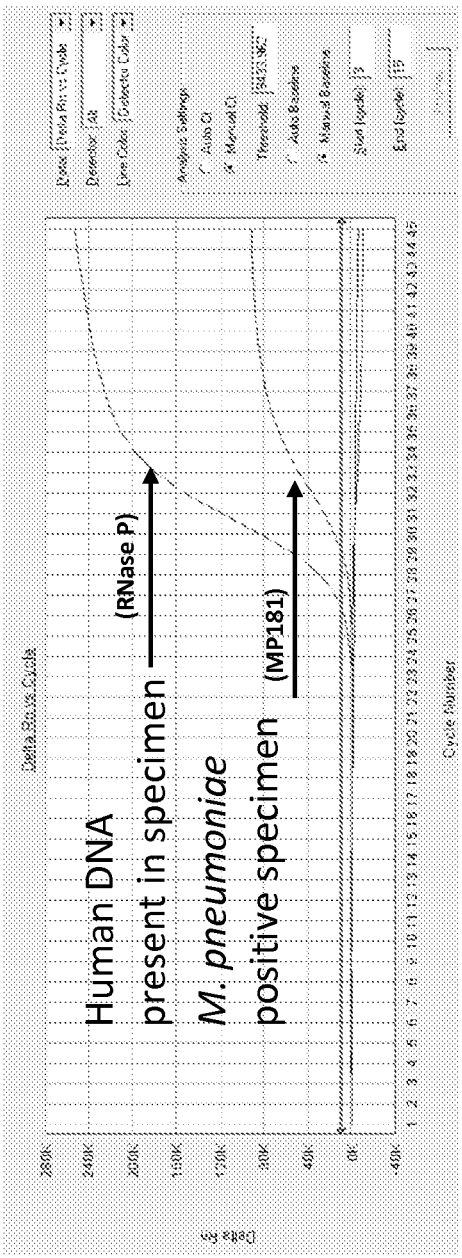
FIG. 2 is a series of digital images showing results of multiplex real-time PCR for clinical specimens positive for *M. pneumoniae* (A), *C. pneumoniae* (B), *Legionella* spp. (C), and a negative specimen (D). Each reaction shows amplification of RNase P from human DNA present in the specimen, indicating successful amplification and detection of nucleic acids in the sample.
Figure 2B:
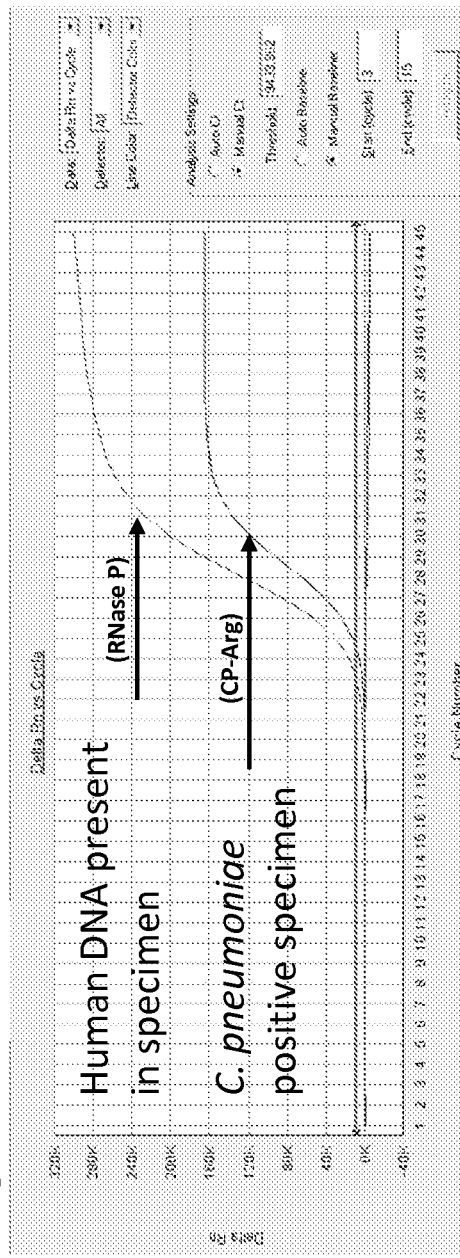
Figure 2C:
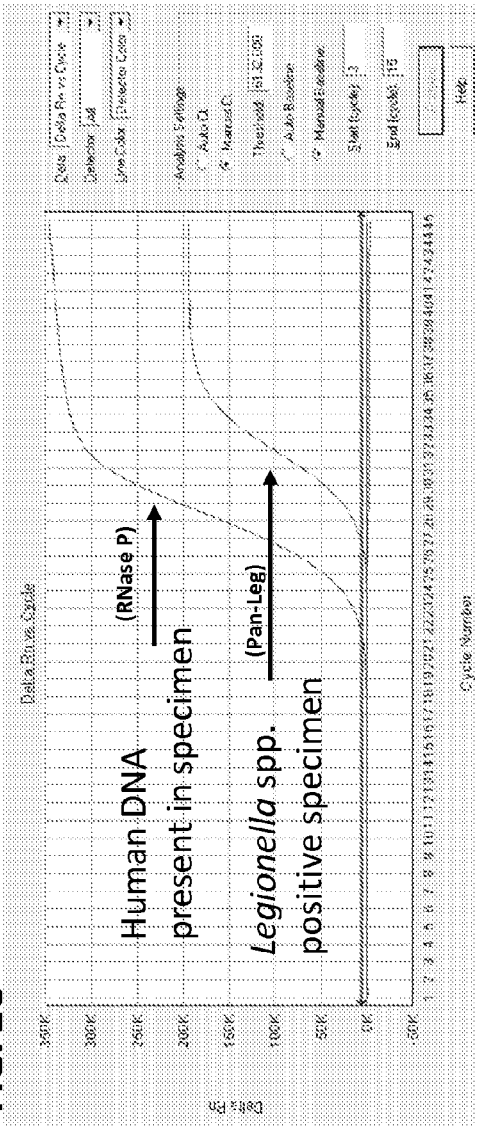
Figure 2D:
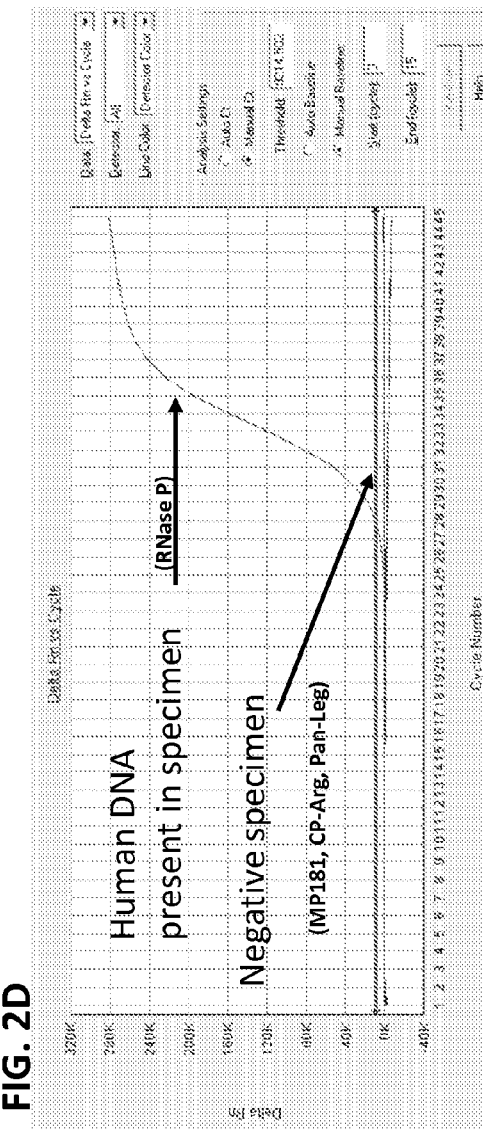

*Two of three replicates had positive $C_t$ values
**One of three replicates had positive $C_t$ values During instrument set up each primer and probe set was assigned a distinct detector color and analysis was performed accordingly. FIG. 1A is an example of positive growth curves for all four markers using the CPC. FIG. 1B is an example of a no template control reaction (NTC) showing no amplification in any of the four assays. Representative positive clinical specimen results are shown in FIGS. 2A-C. A typical negative specimen is shown in FIG. 2D where only RNase P exhibits a positive growth curve, thus validating successful nucleic acid extraction of the clinical specimen.

EXAMPLE 3

Diagnostic Multiplex PCR Assay

This example describes exemplary methods that can be used to detect M. pneumoniae, C. pneumoniae, and/or Legionella spp. nucleic acids in a sample from a subject, thereby diagnosing the subject with infection with the detected organism(s). However, one skilled in the art will appreciate that methods that deviate from these specific methods can also be used to successfully M. pneumoniae, C. pneumoniae, and/or Legionella spp. nucleic acids in a sample and determine a diagnosis for the subject.

Clinical samples are obtained from a subject (such as a subject suspected of having a CAP infection), such as a nasopharyngeal, oropharyngeal, or bronchial swab, bronchoalveolar lavage, or sputum. DNA is extracted from the sample using routine methods (for example using a commercial kit).

Multiplex real-time PCR is performed in a reaction including a reaction mix (e.g., buffers, MgCl$_2$, dNTPs, and DNA polymerase), sample DNA (5 μl of nucleic acid extracted from the sample), and probes and primers. The probes and primers are included in the reaction as follows: 250 nM each for MP181-F (SEQ ID NO: 5), MP181-R (SEQ ID NO: 6), CP-Arg-F (SEQ ID NO: 8), CP-Arg-R (SEQ ID NO: 9), RNaseP-F (SEQ ID NO: 14), and RNaseP-R (SEQ ID NO: 15); 125 nM each for Pan-Leg-F (SEQ ID NO: 11) and Pan-Leg-R (SEQ ID NO: 12); 100 nM for MP-181-P (SEQ ID NO: 7); 50 nM each for CP-Arg-P (SEQ ID NO: 10) and RNaseP-P (SEQ ID NO: 16); and 25 nM for Pan-Leg-P (SEQ ID NO: 13). Probes are labeled as follows: MP181-P (SEQ ID NO: 7), 5'-HEX and 3'-BHQ1; CP-Arg-P (SEQ ID NO: 10), 5'-Quasar 670 and 3'-BHQ3; Pan-Leg-P (SEQ ID NO: 13), 5'-FAM and 3'-BHQ1; and RNaseP-P (SEQ ID NO: 16), 5'-Cal Fluor Red 610 and 3'-BHQ2. The assay is performed using a real-time PCR system (such as the ABI 7500). Exemplary thermocycling conditions are 5 minutes at 95° C., followed by 45 cycles of 95° C. for 15 seconds and 60° C. for 1 minute. Positive samples are those with a positive $C_t$ value for one or more bacterial probes.

EXAMPLE 4

Detection of *M. pneumoniae* in a Clinical Sample

Total nucleic acid was extracted from bacterial isolates and specimens (nasopharyngeal or oropharyngeal specimens) using the InviMag® Bacteria DNA Kit (Invitek, Germany) and the KingFisher® mL extraction platform (Thermo Scientific, Waltham, Mass.) using the InviMag Viral settings. The procedure was performed according to manufacturer's instructions unless otherwise stated. Briefly, 200 µl of viral transport media (VTM) containing nasopharyngeal swabs were incubated in a lysis buffer which includes a proprietary mix of digestive enzymes for 10 min at 65° C. followed by 10 min at 95° C. Approximately 30 mm³ of lung tissue or 125 mm³ of sputum were lysed in the same lysis buffer, but the incubation at 65° C. was increased to overnight. Lysed samples were extracted using the KingFisher® mL platform as recommended by the manufacturer with the elution volume of 260 µl. The samples were centrifuged for one minute at maximum speed to collect leftover beads in the bottom of each tube. Isolated total nucleic acid was stored at −80° C.

*M. pneumoniae* orf521 primers and probe (Mp) were designed manually targeting the orf521 gene (GenBank accession number U43738; nucleotides 10624-12189). Mp primer and probe sequences are shown in Table 3. For real-time PCR, the probe was labeled as follows: 5'-FAM and 3'-BHQ1.

TABLE 3

*M. pneumoniae* orf521 real-time PCR primers and probe

| Primer/<br>Probe | Sequence (5' to 3') | SEQ<br>ID<br>NO: |
|---|---|---|
| Mp-F | AAGAAGCTTATGGTACAGGTTGGTTAA | 19 |
| Mp-R | TGGAGGTTGGTAGCTAAGTAAGCA | 20 |
| Mp-P | TGACTGGAAGGA<u>T</u>GTTAAGCAGGACAACAAATTT<sup>a</sup> | 21 |

<sup>a</sup>Underlined base indicates a locked nucleic acid

Real-time PCR reactions were performed on the Applied Biosystems 7900HT real-time PCR platform in a 96-well format using the AgPath-ID™ One-Step Kit (Applied Biosystems, Foster City, Calif.). Each reaction contained 1× RT-PCR buffer, 1× RT-PCR enzyme, 1× primer and probe mix, 5 µl of total nucleic acid in a total volume of 25 µl. Primers and probes for each assay were premixed, aliquoted and stored at −20° C. until use. All reaction master mixes were prepared and aliquoted into 96-well plates in a clean room to limit the possibility of contamination with template or PCR products. Template was subsequently added to the pre-aliquoted master mix in another room. The plates were sealed, centrifuged at 750×g for 2 minutes, and placed in the thermal cycler. The following cycling conditions were used: 45° C. for 10 min, 94° C. for 10 min, and 45 cycles of 94° C. for 30 sec followed by 60° C. for 1 min.

Limits of detection were determined by analyzing 10-fold serial dilutions of *M. pneumoniae* nucleic acid to determine the lowest detectable concentration range where at least three of four replicates tested positive.

*M. pneumoniae* was successfully detected in clinical specimens. The limit of detection was 00.6-06 genome equivalents/µl.

EXAMPLE 5

Diagnostic Microfluidic Card Assay

This example describes exemplary methods that can be used to detect *M. pneumoniae, C. pneumoniae*, and/or *Legionella* spp. nucleic acids in a sample from a subject, thereby diagnosing the subject with infection with the detected organism(s). However, one skilled in the art will appreciate that methods that deviate from these specific methods can also be used to successfully *M. pneumoniae, C. pneumoniae*, and/or *Legionella* spp. nucleic acids in a sample and determine a diagnosis for the subject.

Clinical samples are obtained from a subject (such as a subject suspected of having a CAP infection), such as a nasopharyngeal, oropharyngeal, or bronchial swab, bronchoalveolar lavage, or sputum. Nucleic acids (such as DNA, RNA, or total nucleic acid) is extracted from the sample using routine methods (for example using a commercial kit).

A microfluidic card (such as a TaqMan® Low Density Array card; Applied Biosystems, Foster City, Calif.) including primers and probes for each of *M. pneumoniae, C. pneumoniae*, and/or *Legionella* spp. is utilized. Individual wells of the card include primers and probe for a single pathogen, which are preloaded and dried onto the designated wells (for example in duplicate). The card includes at least one well containing MP181-F (SEQ ID NO: 5), MP181-R (SEQ ID NO: 6), and MP-181-P (SEQ ID NO: 7) or at least one well containing MpF (SEQ ID NO: 19), MpR (SEQ ID NO: 20), and MpP (SEQ ID NO: 21), labeled with 5'-FAM and 3'BHQ1); at least one well containing CP-Arg-F (SEQ ID NO: 8, labeled with 5'-HEX and 3'-BHQ1), CP-Arg-R (SEQ ID NO: 9), and CP-Arg-P (SEQ ID NO: 10; labeled with 5'-Quasar 670 and 3'-BHQ3); at least one well containing Pan-Leg-F (SEQ ID NO: 11), Pan-Leg-R (SEQ ID NO: 12), and Pan-Leg-P (SEQ ID NO: 13, labeled with 5'-FAM and 3'-BHQ1); and in some cases at least one well containing RNaseP-F (SEQ ID NO: 14), RNaseP-R (SEQ ID NO: 15), and RNaseP-P (SEQ ID NO: 16, labeled with 5'-Cal Fluor Red 610 and 3'-BHQ2) as a positive control. One of skill in the art can select different labels and quenchers with only routine testing.

A master mix, including 1×RT-PCR buffer, 1×RT-PCR enzyme and nucleic acids isolated from a clinical sample is applied to the microfluidic card utilizing the loading ports. The cards are centrifuged, sealed, and placed in a thermocycler (such as the Applied Biosystems 7900HT real-time PCR platform). Cycling conditions are 45° C. for 10 minutes, 94° for 10 minutes, and 45 cycles of 94° C. for 30 seconds and 60° C. for 1 minute (although these conditions can be adjusted by one of skill in the art to obtain optimal results). Positive samples are those with a positive $C_t$ value for one or more bacterial probes.

In view of the many possible embodiments to which the principles of the disclosure may be applied, it should be recognized that the illustrated embodiments are only examples and should not be taken as limiting the scope of the invention. Rather, the scope of the invention is defined by the following claims. We therefore claim as our invention all that comes within the scope and spirit of these claims.

We claim:

1. A method for detecting presence of one or more of a *Mycoplasma pneumoniae* nucleic acid, a *Chlamydophila pneumoniae* nucleic acid, and a *Legionella* spp. nucleic acid in a sample, comprising:

performing hybridization by contacting the sample with a first probe consisting of the nucleotide sequence of SEQ ID NO: 7 and a detectable label; a second probe consisting of the nucleotide sequence of SEQ ID NO: 10 and a detectable label; and a third probe consisting of the nucleotide sequence of SEQ ID NO: 13 and a detectable label or consisting of the nucleotide sequence of SEQ ID NO: 17 and a detectable label; and detecting hybridization between one or more detectably labeled probe and a nucleic acid by detecting a change in signal from one or more detectably labeled probe during or after hybridization relative to signal from the label before hybridization, wherein detection of hybridization between the first probe and a nucleic acid indicates the presence of *M. pneumoniae* nucleic acid in the sample, detection of hybridization between the second probe and a nucleic acid indicates the presence of *C. pneumoniae* nucleic acid in the sample, and detection of hybridization between the third probe and a nucleic acid indicates the presence of *Legionella* spp. nucleic acid in the sample.

2. The method of claim 1, further comprising: contacting the sample with a fourth probe consisting of the nucleic sequence of SEQ ID NO: 16 and a detectable level; and detecting hybridization between the fourth probe and nucleic acid indicating the presence of human ribonuclease P nucleic acid in the sample.

3. The method of claim 1, wherein the first probe consists of X-TGTACCAGAGCACCCCAGAAGGGCT-Y (SEQ ID NO: 7), wherein X is a donor fluorophore and Y is an acceptor fluorophore.

4. The method of claim 1, wherein the second probe consists of X-CTTCAACAGAGAAGACCACGAC-CCGTCA-Y (SEQ ID NO: 10), wherein X is a donor fluorophore and Y is an acceptor fluorophore.

5. The method of claim 1, wherein the third probe consists of X-ACGTGGGTTGC-Y (SEQ ID NO: 13), or X-ACGAT-GAAAACTTTGCTGGTG-Y (SEQ ID NO: 17), wherein X is a donor fluorophore and Y is an acceptor fluorophore.

6. The method of claim 2, wherein the fourth probe consists of X-TTCTGACCTGAAGGCTCTGCGCG-Y (SEQ ID NO: 16), wherein X is a donor fluorophore and Y is an acceptor fluorophore.

7. The method of claim 1, further comprising amplifying one or more of a *Mycoplasma pneumoniae* nucleic acid, a *Chlamydophila pneumoniae* nucleic acid, and a *Legionella* spp. nucleic acid in the sample by real-time polymerase chain reaction:

wherein amplifying the *M. pneumoniae* nucleic acid comprises contacting the sample with a primer consisting of the nucleotide sequence of SEQ ID NO: 5 and a primer consisting of the nucleotide sequence of SEQ ID NO: 6;

wherein amplifying the *C. pneumoniae* nucleic acid comprises contacting the sample with a primer consisting of the nucleotide sequence of SEQ ID NO: 8 and a primer consisting of the nucleotide sequence of SEQ ID NO: 9; and wherein amplifying the *Legionella* spp. nucleic acid comprises contacting the sample with a primer consisting of the nucleotide sequence of SEQ ID NO: 11 and a primer consisting of the nucleotide sequence of SEQ ID NO: 12.

8. The method of claim 7, further comprising amplifying a human ribonuclease P nucleic acid, comprising contacting the sample with a primer consisting of the nucleotide sequence of SEQ ID NO: 14 and a primer consisting of the nucleotide sequence of SEQ ID NO: 15.

9. The method of claim 1, wherein the sample comprises a biological sample from a subject.

10. The method of claim 1, wherein detecting hybridization between one or more detectably labeled probe and a nucleic acid comprises real-time PCR or quantitative real-time PCR.

11. A method for detecting presence of one or more of a *Mycoplasma pneumoniae* nucleic acid, a *Chlamydophila pneumoniae* nucleic acid, and a *Legionella* spp. nucleic acid in a sample, comprising:

amplifying the sample by contacting the sample with a set of primers, wherein the set of primers consist of SEQ ID Nos: 5-6, 8-9, 11-12, and 14-15, to produce amplified fragments that comprise amplified fragments of at least one of the group consisting of *Mycoplasma* pneumonia CARDS toxin, *Chlamydophila pneumoniae* ArgR, *Legionella* ssp. SssA, and human ribonuclease P; and performing a hybridization by simultaneously contacting the amplified fragments with a first probe consisting of the nucleotide sequence of SEQ ID NO: 7 and a detectable label; a second probe consisting of the nucleotide sequence of SEQ ID NO: 10 and a detectable label; a third probe consisting of the nucleotide sequence of SEQ ID NO: 13 and a detectable label and a fourth probe consisting of the nucleotide sequence of SEQ ID NO: 16 and a detectable label, wherein detection of hybridization between the first probe and a nucleic acid indicates the presence of *M. pneumoniae* nucleic acid in the sample, detection of hybridization between the second probe and a nucleic acid indicates the presence of *C. pneumoniae* nucleic acid in the sample, detection of hybridization between the third probe and a nucleic acid indicates the presence of *Legionella* spp. nucleic acid in the sample, and detection of hybridization between the fourth probe and a nucleic acid indicates the presence of human ribonuclease P nucleic acid in the sample.

\* \* \* \* \*